US011352421B2

(12) United States Patent
Hallab et al.

(10) Patent No.: US 11,352,421 B2
(45) Date of Patent: Jun. 7, 2022

(54) TREATMENT FOR ADVERSE IMMUNE REACTION TO METAL IMPLANT DEBRIS

(71) Applicant: RUSH UNIVERSITY MEDICAL CENTER, Chicago, IL (US)

(72) Inventors: Nadim James Hallab, Oak Park, IL (US); Lauryn A. Samelko, Chicago, IL (US); Joshua J. Jacobs, Wilmette, IL (US)

(73) Assignee: RUSH UNIVERSITY MEDICAL CENTER, Chicago, IL (US)

( * ) Notice: Subject to any disclaimer, the term of this patent is extended or adjusted under 35 U.S.C. 154(b) by 130 days.

(21) Appl. No.: 16/216,159

(22) Filed: Dec. 11, 2018

(65) Prior Publication Data

US 2020/0181253 A1    Jun. 11, 2020

(51) Int. Cl.
| | | |
|---|---|---|
| *C07K 16/24* | (2006.01) | |
| *A61K 39/395* | (2006.01) | |
| *A61K 45/06* | (2006.01) | |
| *A61P 37/06* | (2006.01) | |
| *A61K 31/00* | (2006.01) | |

(52) U.S. Cl.
CPC .......... *C07K 16/244* (2013.01); *A61K 39/395* (2013.01); *A61K 45/06* (2013.01); *A61P 37/06* (2018.01); *A61K 31/00* (2013.01)

(58) Field of Classification Search
None
See application file for complete search history.

(56) References Cited

U.S. PATENT DOCUMENTS

| 8,835,610 B2 * | 9/2014 | Hsieh .................. A61P 21/02 530/388.23 |
| 10,588,681 B2 | 3/2020 | Hallab |
| 2016/0175387 A1 | 6/2016 | Bahrami et al. |
| 2017/0056536 A1 | 3/2017 | Hallab et al. |

FOREIGN PATENT DOCUMENTS

| WO | WO2017023929 A1 | 2/2017 |
| WO | WO2017054831 A1 | 4/2017 |

OTHER PUBLICATIONS

Burton et al; Journal of Orthopaedic Research, 2013; vol. 31, pp. 73-80.*
Caicedo et al., Increasing both CoCrMo-Alloy Particle Size and Surface Irregularity Induces Increased Macrophage Inflammasome Activation In vitro Potentially Through Lysosomal Destabilization Mechanisms, J. Orthop. Res. 31(10): 1633-1642 (2013).
Hallab and Jacobs, Chemokines Associated with Pathologic Responses to Orthopedic Implant Debris, Front. Endocrinol. 8:5. doi: 10.3389/fendo.2017.00005 (2017).
Hallab et al., Lymphocyte responses in patients with total hip arthroplasty, J. Orthopaed. Res. 23(2): 384-391 (2005).
Jacobs and Hallab, Loosening and Osteolysis Associated with Metal-on-Metal Bearings: A Local Effect of Metal Hypersensitivity?, J. Bone Surg. 88-A(6): 1171-1172 (2006).
Kwon, et al., Lymphocyte Proliferation Responses in Patients with Pseudotumors following Metal-on-Metal Hip Resurfacing Arthroplasty, J. Orthop. Res. 28(4):444-50. doi: 10.1002/jor.21015 (2010).
Landgraeber, et al., CoCrMo alloy vs. UHMWPE Particulate Implant Debris Induces Sex Dependent Aseptic Osteolysis Responses In Vivo using a Murine Model, Open Orthopaedics Journal, 12:115-124 doi: 10.2174/1874325001812010115 (2018).
Landgraeber, et al., The Pathology of Orthopedic Implant Failure Is Mediated by Innate Immune System Cytokines, Mediators Inflammation 2014, Article ID 185150, 1-9, http://dx.doi.org/10.1155/2014/185150 (2014).
Samelko et al., Cobalt Alloy Implant Debris Induces Inflammation and Bone Loss Primarily through Danger Signaling, Not TLR4 Activation: Implications for DAMP-ening Implant Related Inflammation, PLoS One 11(7): e0160141 (2016).
Samelko, et al., Is IL-1 Signaling Essential for Promoting TH17-cell Induced Metal Hypersensitivity Immune Responses?, Paper No. 0174, Orthopaedic Research Society Annual Meeting, San Diego, CA, Mar. 19-22, 2017.
Samelko, et al., Is Blocking IL-17 a Viable Treatment for Metal-induced Delayed Type Hypersensitivity Responses to Implant Debris?, Paper No. 0221, Orthopaedic Research Society Annual Meeting, New Orleans, LA, Mar. 10-13, 2018.
Caicedo et al., "Females with Unexplained Joint Pain Following Total Joint Arthroplasty Exhibit a Higher Rate and Severity of Hypersensitivity to Implant Metals Compared with Males: Implications of Sex-Based Bioreactivity Differences," J Bone Joint Surg Am., vol. 99, No. 8, (2017), pp. 621-628.
Caicedo et al., "Metal Sensitivities Among TJA Patients with Post-Operative Pain: Indications for Multi-Metal LTT Testing," J Long Term Eff Med Implants, vol. 24, No. 1, (2014), pp. 37-44.
Hallab et al., "Biologic effects of implant debris," Bull NYU Hosp Jt Dis. 2009;67(2):182-8.
Hallab et al., "Biomaterial optimization in total disc arthroplasty," Spine, Oct. 15, 2003;28(20):S139-52.
Hallab et al., "Immune responses correlate with serum-metal in metal-on-metal hip arthroplasty," J Arthroplasty Dec. 2004;19(8 Suppl 3):88-93.

(Continued)

*Primary Examiner* — Bridget E Bunner
*Assistant Examiner* — Fozia M Hamud
(74) *Attorney, Agent, or Firm* — Barnes & Thornburg LLP

(57) ABSTRACT

Described herein is a method for treating or prophylaxis of adverse immune reaction to metal debris, metal induced delayed type hypersensitivity (DTH), or inflammatory osteolysis by attenuating the inflammatory response. In one aspect, the method involves inhibiting the nucleotide-binding domain (NOD)-like receptor protein 3 (NLRP3) inflammasome/caspase-1 pathway or neutralizing or blocking the activity of interleukin 17 (IL-17), IL-17 receptor (IL-17R), IL-1R, IL-1β, IL-18, IL-21, IL-23 with anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, inflammasome inhibitors, or combinations thereof.

21 Claims, 14 Drawing Sheets

(56) References Cited

OTHER PUBLICATIONS

Hallab et al., "In vitro reactivity to implant metals demonstrates a person-dependent association with both T-cell and B-cell activation," J Biomed Mater Res A. Feb. 2010;92(2):667-82.
Hallab et al., "The Inflammatory Effects of Breast Implant Particulate Shedding: Comparison With Orthopedic Implants," Aesthet Surg J. Jan. 31, 2019;39(Suppl_1):S36-S48.
Hallab, "A review of the biologic effects of spine implant debris: Fact from fiction," Sas J. Dec. 1, 2009;3(4):143-60.
Hallab, "Lymphocyte Transformation Testing for Quantifying Metal-Implant-Related Hypersensitivity Responses," Dermatitis, vol. 15, No. 2, (2004), pp. 82-90.
Samelko et al., "Is IL-1 Signaling Essential for Promoting TH17-Cell Induced Metal Hypersensitivity Immune Responses?" ORS Annual Meeting Paper No. 0174 (2017).
Samelko et al., "Transition from metal-DTH resistance to susceptibility is facilitated by NLRP3 inflammasome signaling induced Th17 reactivity: Implications for orthopedic implants," PLoS One. Jan. 17, 2019;14(1).
Scholz et al., "Renal Dendritic Cells Stimulate IL-10 Production and Attenuate Nephrotoxic Nephritis," J Am Soc Nephrol., vol. 19, No. 3, (2008), pp. 527-537.
Summer et al., "Nickel (Ni) Allergic Patients with Complications to Ni Containing Joint Replacement Show Preferential IL-17 Type Reactivity to Ni," Contact Dermatitis, vol. 63, No. 1, (2010), pp. 15-22.

\* cited by examiner

| | Sensitization | Challenge | DTH Analysis |
|---|---|---|---|
| | D1, D10 | D12 | D14 |
| | 1. Vehicle | 1. $NiCl_2$+ CFA | 1. Paw thickness |
| | 2. DTH | 2. $NiCl_2$+ CFA | 2. Cell proliferation |
| | | | 3. Cytokine |

TREATMENT FOR ADVERSE IMMUNE REACTION TO METAL IMPLANT DEBRIS

GOVERNMENT INTEREST

This invention was made with United States government support under National Institutes of Health/National Institute of National Institute of Arthritis and Musculoskeletal and Skin Diseases grant numbers AR 060782. The United States government has certain rights in the invention.

TECHNICAL FIELD

Described herein is a method for treating or prophylaxis of adverse immune reaction to metal debris, metal induced delayed type hypersensitivity (DTH), or inflammatory osteolysis by attenuating the inflammatory response. In one aspect, the method involves inhibiting the nucleotide-binding domain (NOD)-like receptor protein 3 (NLRP3) inflammasome/caspase-1 pathway or neutralizing or blocking the activity of interleukin 17 (IL-17), IL-17 receptor (IL-17R), IL-1R, IL-1β, IL-18, IL-21, IL-23 with anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, inflammasome inhibitors, or combinations thereof.

BACKGROUND

Metal hypersensitivity associated with total joint replacement (TJR) remains an incompletely understood phenomenon. There are numerous documented cases and group studies demonstrating metal-implant related adaptive immune reactivity responses, identified histologically by increased peri-implant lymphocyte infiltrations/accumulations similar to vaccine recall responses. Thomas et al., *Allergy* 64(8): 1157-1165 (2009). Adaptive immune responses have been associated in metal-on-metal (MoM) hip arthroplasty failures, where variability in biological responses to metal debris in vivo has shown to be a main contributor to poor functioning implants in certain subjects. Kwon et al., *J. Orthop. Res.* 28(4): 444-550 (2010). Metal debris generated from metallic implant components can activate the immune system. The two best known metal immune sensitizers are nickel and cobalt. Merritt et al., *Clin. Orthop. Rel. Res.* 326: 71-79 (1996). Metal sensitivity reactions have been found to occur in 20% of individuals with well-performing TJRs and in 60% of individuals experiencing poorly functioning implants. Hallab et al., *J. Orthop. Res.* 23(2): 384-391 (2005); Jacobs and Hallab, *J. Bone Joint Surg. Am.* 88(6): 1171-1172 (2006). However, therapeutic options for orthopedic implant associated metal hypersensitivity remain unidentified. There is increasing evidence that suggests that IL-17A is an important adaptive immune cytokine that is significantly increased in metal-reactive individuals. Samelko et al., Paper No. 0174, Orthopaedic Research Society Annual Meeting, San Diego Calif., Mar. 19-22, 2017. Thus, IL-17 activity appears to be important for the pathogenesis of metal delayed-type hypersensitivity (DTH) responses.

What is needed is a method for prophylaxis or treatment of adverse immune reaction to metal debris, metal induced delayed type hypersensitivity (DTH), or inflammatory osteolysis by modulating the inflammatory response.

SUMMARY

One embodiment described herein is a method for treating or prophylaxis of adverse immune reaction to metal debris, metal induced delayed type hypersensitivity, or inflammatory osteolysis in a subject in need thereof comprising inhibition of the NLRP3 inflammasome pathway or IL-17 activity. In one aspect, inhibition is effectuated by the administration of an effective amount of one or more anti-cytokine antibodies, anti-receptor antibodies, soluble receptors, blocking agents, or inflammasome inhibitors to the subject. In another aspect, the anti-cytokine antibodies, anti-receptor antibodies, soluble receptors, or blocking agents comprise anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, or combinations thereof. In another aspect, the anti-cytokine antibodies, anti-receptor antibodies, soluble receptors, blocking agents comprise secukinumab, ixekizumab, brodalumab, anakinra, rilonacept, canakinumab, or combinations thereof. In another aspect, the inflammasome inhibitors comprise chloroquine, metformin, glybenclamide, methotrexate, ibrutinib (IMBRUVICA®), sβ-485232 (GSK), β-hydroxybutyrate, interferon α, interferon β, resveratrol, arglabin, CB2R agonist, VX-765, Ac-YVAD-cmk, bafilomycin A1, isoliquiritigenin, MCC950, parthenolide, pepinh-MYD, Bay11-7082 NLRP3, Z-VAD-FMK, other BTK inhibitors, other autophagy inducers, other caspase-1 inhibitors, other inflammasome inhibitors, or combinations thereof. In another aspect, the anti-cytokine antibodies, anti-receptor antibodies, soluble receptors, blocking agents, or inflammasome inhibitors are co-administered.

Another embodiment described herein is a method for depleting a subject's systemic levels of IL-17 or blocking a IL-17 receptor comprising contacting IL-17 or IL-17 receptors with anti-IL-17, anti-IL-17A, anti-IL-17F, anti-IL-17A/F, anti-IL-1, anti-IL-1β, anti-IL-1R, soluble IL-17 receptors, IL-17 receptor inhibitors, blocking agents, or combinations thereof. In one aspect, the contacting comprises parenteral administration of one or more of anti-cytokine antibodies, anti-receptor antibodies, soluble receptors, or blocking agents. In another aspect, the parenteral administration comprises intravenous, intraarterial, intramuscular, intraarticular, intradermal, subcutaneous, or intraperitoneal administration. In another aspect, the subject is experiencing adverse immune reaction to metal debris, metal induced delayed type hypersensitivity, or inflammatory osteolysis.

Another embodiment described herein is a method for inhibiting the NLRP3 inflammasome pathway or IL-17 activity in a subject experiencing adverse immune reaction to metal debris, metal induced delayed type hypersensitivity, or inflammatory osteolysis by the administration of one or more anti-cytokine antibodies, anti-receptor antibodies, soluble receptors, blocking agents, or inflammasome inhibitors to the subject. In one aspect, the anti-cytokine antibodies, anti-receptor antibodies, soluble receptors, or blocking agents comprise anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, or combinations thereof. In another aspect, the anti-cytokine antibodies, anti-receptor antibodies, soluble receptors, blocking agents comprise secukinumab, ixekizumab, brodalumab, anakinra, rilonacept, canakinumab, or combinations thereof. In another aspect, the inflammasome inhibitors comprise chloroquine, metformin, glybenclamide, methotrexate, ibrutinib (IMBRUVICA®), sβ-485232 (GSK), β-hydroxybutyrate, interferon α, interferon β, resveratrol, arglabin, CB2R agonist, VX-765, Ac-YVAD-cmk, bafilomycin A1, isoliquiritigenin, MCC950, parthenolide, pepinh-MYD, Bay11-7082 NLRP3, Z-VAD-FMK, other BTK inhibitors, other autophagy inducers, other caspase-1 inhibitors, other inflammasome inhibitors, or combinations thereof. In another aspect, the anti-cytokine antibodies, anti-receptor antibodies, soluble receptors, blocking agents, or inflammasome inhibitors are co-administered.

Another embodiment described herein is a method for blocking intracellular effects of IL-17 or IL-1R by contacting one or more of IL-17, IL-17R, IL-1R, IL-1β, IL-18, IL-21, IL-22 with anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, or combinations thereof.

Another embodiment described herein is a composition comprising one or more anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, or combinations thereof; and optionally, one or more pharmaceutically acceptable excipients.

Another embodiment described herein is a kit for inhibiting the NLRP3 inflammasome pathway or IL-17 activity comprising one or more receptacles comprising anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, inflammasome inhibitors, or a combination thereof, and optionally, a delivery device, a diluent, instructions for use, or a label.

BRIEF DESCRIPTION OF THE DRAWINGS

FIGS. 1D and 1E demonstrate inflammatory lymphocytic infiltrations (arrows) found in the paw tissue of DTH mice.

DETAILED DESCRIPTION

Figure 1A:
FIG. 1A. Schematic model for generating metal-DTH to orthopedic implant metal(s) in vivo.

One embodiment described herein is a method for treating or prophylaxis of adverse immune reaction to metal debris, metal induced delayed type hypersensitivity, or inflammatory osteolysis in a subject in need thereof comprising inhibition of the NLRP3 inflammasome pathway or IL-17 activity.

As used herein the terms "cytokine" or "cytokines" refer to the interleukins, interferons, tumor necrosis factor (TNF), NF-κB, growth factors, or other molecules that can exert an effect on a cell or other cells. In some aspect, cytokine refers to IL-17, IL-17A, IL-17F, IL-17A/F, IL-1, IL-1β, IL-21, IL-23, among others.

As used herein the term "receptor" refers to receptors of cytokines or other molecules, such as interleukin 17 receptor, interleukin 1 receptor, or other cell surface receptors.

As used herein, the term "soluble receptor" refers to a receptor, typically recombinant, that can interact with a cytokine. Examples include soluble IL-17 receptor (IL-17R) or IL-1 receptor (IL-1R). In addition, the term soluble receptor also refers to an alternative to an anti-cytokine antibody.

As used herein the terms "anti-cytokine antibodies," or "anti-cytokine antibody" refer to antibodies that recognize one or more cytokines or effector proteins, such as interleukins, interferons, tumor necrosis factor (TNF), NF-κB, growth factors, or other molecules that can exert an effect on other cells. The antibodies may be natural, polyclonal, monoclonal, single chain, recombinant, or humanized. Humanized antibodies are particularly useful.

As used herein the terms "anti-receptor antibodies," or "anti-receptor antibody" refer to antibodies that recognize one or more cytokine receptor molecules such anti-interleukin 1 receptors (anti-IL-1R) or other cytokine or cell surface receptors.

As used herein the term "blocking agent" refers to a molecule that can interact with a cytokine, cytokine receptor, soluble receptor, cell-surface receptor, inflammasome, or the like and inhibit its natural function. Typically, inhibition involves blocking the ability of the molecule to bind its receptor or natural ligand. Blocking agents may be biomolecules such as proteins or small molecules.

As used herein, the terms "treatment", "treat," and "treating" refers a course of action (such as administering a compound or pharmaceutical composition) initiated after the onset of a symptom, aspect, or characteristics of a disease or condition so as to eliminate or reduce such symptom, aspect, or characteristics. Such treating need not be absolute to be useful.

As used herein, the terms "in need thereof" or "in need of treatment" refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

The terms "subject" or "patient" as used herein refers to any animal, including mammals, such as mice, rats, other rodents, rabbits, dogs, cats, swine, cattle, sheep, horses, non-human primates, or humans. In one aspect, the subject is a human. In another aspect, the subject is a human child or adult. In another aspect, the subject is in need treatment or in need of thereof.

As used herein, the term "therapeutically effective amount" refers to an amount of a compound, either alone or as a part of a single or multi-agent pharmaceutical composition, that is capable of having any detectable, positive effect on any symptom, aspect, or characteristics of a disease or condition. Such effect need not be absolute to be beneficial or useful. When referring to an anti-cytokine antibody, anti-receptor antibody, soluble receptor, or blocking agent, the term "therapeutically effective amount" refers to an amount of such species sufficient to attenuate, inhibit, or stem metal induced delayed type hypersensitivity or inflammatory osteolysis. The therapeutically effective amount will vary for each anti-cytokine antibody, anti-receptor antibody, soluble receptor, or blocking agent. For example, a composition comprising two specific anti-cytokine antibodies, will potentially have two independent therapeutically effective amounts—one for each anti-cytokine antibody.

The terms "about" and "approximately" as used herein refer an acceptable degree of error or variation for the quantity measured given the nature or precision of the measurements. Typical, exemplary degrees of error or variation are within 20% or within 10% of a given value or range of values. For biological systems, the term "about" refers to an acceptable standard deviation of error, preferably not more than 2-fold of a give value. Numerical quantities given herein are approximate unless stated otherwise, meaning that the term "about" or "approximately" can be inferred when not expressly stated.

Results described herein show that the pathogenesis of metal hypersensitivity responses to implant debris are largely dependent on activation of the inflammasome/caspase-1 pathway and subsequent production of IL-17A/F by CD4+ T cells both in vivo and in vitro. Inhibiting either the inflammasome pathway or IL-17A (in vivo using NLRP3 and Caspase-1 deficient mice or in vitro using blocking agents such as Capase-1 inhibitor, IL-1Ra, or anti-IL-17A), significantly mitigated metal-DTH paw inflammation ($p<0.05$) as well as lymphocyte cytokine (IFN-γ and IL-17) and proliferation responses in metal-sensitized mice and primary human PBMCs.

One embodiment described herein is a method for treating or prophylaxis of adverse immune reaction to metal debris, metal induced delayed type hypersensitivity, or inflammatory osteolysis in a subject in need thereof comprising inhibition of the NLRP3 inflammasome pathway or IL-17 activity. In one aspect, the inhibition is effectuated by the administration of an effective amount of one or more anti-cytokine antibodies, anti-receptor antibodies, soluble receptors, receptor inhibitors, blocking agents, or inflammasome inhibitors to the subject. In another aspect, the anti-cytokine antibodies, anti-receptor antibodies, soluble receptors, receptor inhibitors, or blocking agents comprise anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, or combinations thereof. In another aspect, the inflammasome inhibitors comprise chloroquine, metformin, glybenclamide, methotrexate, ibrutinib (IMBRUVICA®), sβ-485232 (GSK), β-hydroxybutyrate, interferon α, interferon β, resveratrol, arglabin, CB2R agonist, VX-765, Ac-YVAD-cmk, bafilomycin A1, isoliquiritigenin, MCC950, parthenolide, pepinh-MYD, Bay11-7082 NLRP3, Z-VAD-FMK, other BTK inhibitors, other autophagy inducers, other caspase-1 inhibitors, other inflammasome inhibitors, or combinations thereof. In another aspect, the anti-cytokine antibodies, anti-receptor antibodies, soluble receptors, receptor inhibitors, blocking agents, or inflammasome inhibitors are co-administered. In another aspect, the adverse immune reaction to metal debris, metal induced delayed type hypersensitivity, or inflammatory osteolysis is caused by orthopedic metal implant debris. In another aspect, the orthopedic metal implant debris comprises nickel, cobalt, or chromium. In another aspect, the orthopedic metal implant is associated with total joint arthroplasty. In another aspect, the adverse immune reaction to metal debris, metal induced delayed type hypersensitivity, or inflammatory osteolysis is identified histologically as aseptic lymphocyte-dominated vasculitis-associated lesions (ALVAL) in periprosthetic tissue.

In one embodiment, the administration of the anti-cytokine antibodies, anti-receptor antibodies, soluble receptors, receptor inhibitors, or blocking agents occurs within about 0.5 hour to about 30 days of the onset of metal-induced delayed type hypersensitivity. In one aspect the administration occurs after about 0.5 h 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, or about 24 h of the onset of viral infection. In another aspect, the administration occurs after about 0.1 day, about 0.25 day, about 0.5 day, about 0.75 day, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, or about 31 days. In another aspect, the administration occurs after about 0.1 month, about 0.25 months, about 0.5 months, about 0.75 months, about 1 month, about 2 months, about 3 months, about 4 months, about 5 months, about 6 months, about 7 months, about 8 months, about 9 months, about 10 months, about 11 months, or about 12 months. In another aspect, the administration occurs after about 0.1 year, about 0.25 years, about 0.5 years, about 0.75 years, about 1 year, about 2 years, about 3 years, or about 5 years.

In another embodiment, the administration of the anti-cytokine antibodies, anti-receptor antibodies, soluble receptors, receptor inhibitors, or blocking agents occurs no later than about 7 days after the onset of adverse immune reaction to metal debris, metal-induced delayed type hypersensitivity, or inflammatory osteolysis. In another aspect, the administration occurs no later than about 1 day, about 2 days, about 3 days, about 4 days, about 5 days, about 6 days, or about 7 days after onset of adverse immune reaction to metal debris, metal-induced delayed type hypersensitivity, or inflammatory osteolysis.

In another embodiment, the administration of the anti-cytokine antibodies, anti-receptor antibodies, soluble receptors, receptor inhibitors, or blocking agents is by any means effective to administer the medicaments. In one aspect, the administration comprises parenteral administration. In another aspect, the administration comprises intravenous, intraarterial, intraarticular, intramuscular, intradermal, subcutaneous, or intraperitoneal administration. In another aspect, the administration comprises intravenous administration. In another aspect, the administration comprises intraarticular administration. In another aspect, the administration comprises intravenous infusion.

In another embodiment described herein, the subject is a mouse, rat, other rodent, rabbit, dog, cat, pig, cow, sheep, horse, non-human primate, or human. In one embodiment, the subject is a human or a human in need thereof. In another aspect, the subject is a human child or adult in need thereof. As used herein, the phrase "in need thereof" indicates that the subject is need of treatment as determined by a physician.

Another embodiment described herein is a method for depleting a subject's systemic levels of one or more of cytokines IL-17, IL-17A, IL-17F, IL-17A/F, IL-1, IL-1β, IL-18, IL-21, IL-23, inhibiting the IL-1 receptor (IL-1R), IL-17 receptor, inhibiting other IL receptors, or inhibiting the inflammasome comprising contacting the cytokines or receptors with one or more anti-cytokine antibodies, anti-receptor antibodies, soluble receptors, receptor inhibitors, blocking agents, caspase inhibitors, or inflammasome inhibitors. In one aspect, the contacting comprises parenteral administration of one or more of anti-cytokine antibodies, anti-receptor antibodies, soluble receptors, receptor inhibitors, or blocking agents. In another aspect, the anti-cytokine antibodies, anti-receptor antibodies, soluble receptors, receptor inhibitors, or blocking agents comprise one or more of anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, or combinations thereof. In one aspect, the anti-cytokine antibodies, anti-receptor antibodies, soluble receptors, receptor inhibitors, or blocking agents comprise one or more of secukinumab (COSENTYX®), ixekizumab (TALTZ®), brodalumab (SILIQ™), anakinra (KINERET®), rilonacept (ARCALYST®), and canakinumab (ILARIS®). In another aspect, the caspase inhibitors, or inflammasome inhibitors comprise one or more of comprise chloroquine, metformin, glybenclamide, methotrexate, ibrutinib (IMBRUVICA®), sβ-485232 (GSK), β-hydroxybutyrate, interferon α, interferon β, resveratrol, arglabin, CB2R agonist, VX-765, Ac-YVAD-cmk, bafilomycin A1, isoliquiritigenin, MCC950, parthenolide, pepinh-MYD, Bay11-7082 NLRP3, Z-VAD-FMK, other BTK inhibitors, other autophagy inducers, other caspase-1 inhibitors, other inflammasome inhibitors, or combinations thereof.

In another aspect, the anti-cytokine antibodies, anti-receptor antibodies, soluble receptors, receptor inhibitors, or blocking agents comprise anti-IL-4R, anti-IL-6, anti-IL-6 receptor, anti-TNFα, soluble TNF receptors, anti-IFNγ, or combinations thereof. In another aspect, the anti-cytokine antibodies, anti-receptor antibodies, soluble receptors, receptor inhibitors, or blocking agents comprise infliximab (REMICADE®), adalimumab (HUMIRA®), certolizumab pegol (CIMZIA®), etanercept (ENBREL®), siltuximab (SYLVANT®), tocilizumab (ACTEMRA®), dupilumab (DUPIXENT®), afelimomab, bersanlimab, blazakizumab, fontolizumab, golimumab, nerelimomab, olokizumab, ozoralizumab, pascolizumab, placulumab, sapelizumab, sarilumab, vobarilizumab, combinations thereof, derivatives thereof, or analogues thereof.

In another aspect, the method involves parenteral administration of one or more of anti-cytokine antibodies, anti-receptor antibodies, soluble receptors, receptor inhibitors, caspase inhibitors, inflammasome inhibitors, or blocking agents to the subject which permits the anti-cytokine antibodies, anti-receptor antibodies, soluble receptors, receptor inhibitors, or blocking agents to interact with the cytokine or receptor and neutralize the cytokine or receptor ligand preventing binding and downstream effects. In one aspect, the parenteral administration comprises intravenous administration. In another aspect, the subject is experiencing adverse immune reaction to metal debris, metal induced delayed type hypersensitivity, or inflammatory osteolysis. In one aspect, the subject is a human.

Another embodiment described herein is a method for blocking intracellular effects of IL-17 in response adverse immune reaction to metal debris, metal induced delayed type hypersensitivity, or inflammatory osteolysis in a subject in need thereof comprising administering one or more anti-cytokine antibodies, anti-receptor antibodies, soluble receptors, receptor inhibitors, blocking agents, caspase inhibitors, or inflammasome inhibitors. In another aspect, the anti-cytokine antibodies, anti-receptor antibodies, soluble receptors, receptor inhibitors, or blocking agents comprise one or more of anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, or combinations thereof. In one aspect, the anti-cytokine antibodies, anti-receptor antibodies, soluble receptors, receptor inhibitors, or blocking agents comprise one or more of secukinumab (COSENTYX®), ixekizumab)(TALTZ®), brodalumab (SILIQ™), soluble IL-17 receptors, IL-17 receptor inhibitors, or blocking agents, or combinations thereof. In another aspect, the blocking agent comprises one or more small molecules that are capable of binding to the receptor and blocking interaction with the cytokine or receptor ligand.

Another embodiment described herein is a method for inhibiting the NLRP3 inflammasome pathway or IL-17 activity in a subject experiencing adverse immune reaction to metal debris, metal induced delayed type hypersensitivity, or inflammatory osteolysis by the administration of one or more anti-cytokine antibodies, anti-receptor antibodies, soluble receptors, receptor inhibitors, blocking agents, inflammasome inhibitors or combinations thereof to the subject. In one aspect, the anti-cytokine antibodies, anti-receptor antibodies, soluble receptors, or blocking agents comprise anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, or combinations thereof. In another aspect, the anti-cytokine antibodies, anti-receptor antibodies, soluble receptors, blocking agents comprise secukinumab, ixekizumab, brodalumab, anakinra, rilonacept, canakinumab, or combinations thereof. In another aspect, the inflammasome inhibitors comprise chloroquine, metformin, glybenclamide, methotrexate, ibrutinib (IMBRUVICA®), sβ-485232 (GSK), β-hydroxybutyrate, interferon α, interferon β, resveratrol, arglabin, CB2R agonist, VX-765, Ac-YVAD-cmk, bafilomycin A1, isoliquiritigenin, MCC950, parthenolide, pepinh-MYD, Bay11-7082 NLRP3, Z-VAD-FMK, other BTK inhibitors, other autophagy inducers, other caspase-1 inhibitors, other inflammasome inhibitors, or combinations thereof. In another aspect, the anti-cytokine antibodies, anti-receptor antibodies, soluble receptors, receptor inhibitors, blocking agents, or inflammasome inhibitors are co-administered.

Another embodiment described herein is a pharmaceutical composition comprising a mixture of one or more anti-cytokine antibodies, anti-receptor antibodies, soluble receptors, receptor inhibitors, or blocking agents comprising anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors IL-23 receptor inhibitors; and optionally, one or more pharmaceutically acceptable excipients, vehicles, or dilutants. In one aspect, the composition comprises 1 mg to 10,000 mg of each antibody or receptor. In another aspect, the composition dose is about 0.01 mg/kg to about 200 mg/kg. In another aspect, the composition dose is about 5 mg/kg. In another aspect, the composition is a liquid or a lyophylized concentrate.

Another embodiment described herein is a kit for inhibiting the NLRP3 inflammasome pathway or IL-17 activity comprising one or more receptacles comprising anti-IL-17, anti-IL-17A, anti-IL-17F, anti-IL-17A/F, anti-IL-1, anti-IL-1β, anti-IL-18, anti-IL-21, anti-IL-23, anti-IL-1R, soluble IL-17 receptors, soluble IL-1 receptors, soluble IL-18 receptors, soluble IL-21 receptors, IL-17 receptor inhibitors, IL-1 receptor inhibitors, IL-18 receptor inhibitors, IL-21 receptor inhibitors, IL-23 receptor inhibitors, blocking agents, inflammasome inhibitors, or a combination thereof, and optionally, a delivery device, a diluent, instructions for use, or a label.

Pharmaceutical compositions suitable for administration by injection include sterile aqueous solutions, suspensions, or dispersions and sterile powders or lyophilisates for the extemporaneous preparation of sterile injectable solutions or dispersion.

For intravenous administration, suitable carriers include physiological saline, phosphate buffered saline (PBS), Ringer's solution, or water for injection. In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, buffers, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, or by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, amino acids, sorbitol, sodium chloride, or combinations thereof in the composition. Prolonged absorption of the injectable compositions can be brought about by including in the composition an agent that delays absorption, for example, aluminum monostearate and gelatin.

Certain injectable compositions are aqueous isotonic solutions or suspensions. Such compositions may be sterilized and/or contain adjuvants, such as preservatives, stabilizers, wetting agents, emulsifying agents, solution promoters, salts for regulating the osmotic pressure and/or buffers. In addition, they may also contain other therapeutically valuable substances. Said compositions are prepared according to conventional methods, respectively, and contain about 0.1-75%, or contain about 1-50%, of the active ingredient.

Sterile injectable solutions or suspensions can be prepared by incorporating the anti-cytokine antibodies, anti-receptor antibodies, soluble receptors, receptor inhibitors, or blocking agents in the required amount in an appropriate solvent with one or a combination of ingredients, as required, followed by filtration sterilization. Generally, solutions or suspensions are prepared by incorporating the active compound into a sterile vehicle such as sterile PBS and any excipients. In the case of sterile powders for the preparation of sterile injectable solutions, the preferred preparation methods are vacuum drying and freeze-drying which yields a powder of the active ingredient plus any additional desired ingredient from a previously sterile-filtered solution thereof.

The effective amount of a pharmaceutical composition to be employed therapeutically will depend, for example, upon the therapeutic context and objectives. One skilled in the art will appreciate that the appropriate dosage levels for treatment will thus vary depending, in part, upon the therapeutic agent incorporated into the pharmaceutical composition, the indication for which the therapeutic agent is being used, the route of administration, and the size (body weight, body surface, or organ size) and condition (the age and general health) of the patient. Accordingly, the clinician can titer the dosage and route of administration to obtain the optimal therapeutic effect.

Anti-cytokine antibodies, anti-receptor antibodies, soluble receptors, receptor inhibitors, or blocking agents can be produced using standard monoclonal antibody (particularly humanized monoclonal antibodies) techniques, protein engineering, and general molecular biological techniques know to those having ordinary skill in the art.

Several exemplary FDA-approved anti-cytokine antibodies, anti-receptor antibodies, soluble receptors, receptor inhibitors, or blocking agents useful for the methods described herein include secukinumab (COSENTYX®), ixekizumab (TALTZ®), brodalumab (SILIQ™), anakinra (KINERET®), rilonacept (ARCALYST®), canakinumab (ILARIS®), interferon β (BETASERON®), or combinations thereof, among other agents. Relevant dose and concentration parameters of these agents are provided in Table 1. The FDA prescribing information, i.e., the labels or package inserts for infliximab secukinumab (COSENTYX®), ixekizumab (TALTZ®), brodalumab (SILIQ™), anakinra (KINERET®), rilonacept (ARCALYST®), canakinumab (ILARIS®), interferon β (BETASERON®) and ibrutinib (IMBRUVICA®), are each incorporated herein by express reference thereto for their specific teachings.

TABLE 1

FDA-approved anti-cytokine, anti-receptor antibodies, or soluble receptors

| Therapeutic | Target | Indicated Dose; Total Dose | Concentration, Vol. |
|---|---|---|---|
| Secukinumab (COSENTYX ®) | IL-17A | *2.1-4.2 mg/kg*; 150-300 mg at weeks 0, 1, 2, 4; then every 4 weeks | 150 mg/mL; 1 mL |
| Ixekizumab (TALTZ ®) | IL-17A | *1.1-2.2 mg/kg*; 80-160 mg/2 weeks for 12 weeks, then 80 mg every 4 weeks | 80 mg/mL; 1 mL |
| Brodalumab (SILIQ ™) | IL-17R | *3 mg/kg*; 210 mg every 2 weeks | 140 mg/mL; 1.5 mL |
| Anakinra (KINERET ®) | IL-1 | *1.4 mg/kg*; 100 mg/day | 150 mg/mL; 0.67 mL |
| Rilonacept (ARCALYST ®) | IL-1 | *2.3-4.6 mg/kg*; 320 mg initial, 160 mg weekly | 80 mg/mL; 2 mL |
| Canakinumab (ILARIS ®) | IL-Iβ | *2-4 mg/kg*; 150-300 mg every 4 to 8 weeks | 150 mg/mL; 1 mL |

Italicized doses (mg/kg) were calculated based on the total indicated dose using an average human body mass of 70 kg. Non-italicized doses were provided in the label.

As can be observed from Table 1, the dose of each therapeutic agent varies in its administration dose, recurrent dosing schedule, and concentration.

Other anti-cytokine antibodies, anti-receptor antibodies, or soluble receptors are approved for human use throughout the world. For example the following compounds and their (targets) may be useful for the methods described herein: infliximab (TNF); adalimumab (TNF); certolizumab pegol (TNF); etanercept (TNF); siltuximab (IL-6R); tocilizumab (IL-6R); dupilumab (IL-4R); afelimomab (TNFα); bersanlimab (ICAM-1); clazakizumab (IL-6); fontolizumab (INF-γ); golimumab (TNFα); nerelimomab (TNFα); olokizumab (IL-6); ozoralizumab (TNFα); pascolizumab (IL-4); placulumab (TNF); sapelizumab (IL-6R); sarilumab (IL-6); vobarilizumab (IL-6R), among others, or combinations thereof.

In addition, the commercially available inflammasome inhibitors or blocking agents listed in Table 2 are useful for attenuating the inflammasome response to metal (e.g., InvivoGen, Sigma-Aldrich).

TABLE 2

Inflammasome Inhibitors

| Inhibitor | Activity |
|---|---|
| Chloroquine | Inhibits endosomal acidification |
| Metformin | Activates AMPK |
| Glybenclamide | NLRP3 Inflammasome Inhibitor; proton pump inhibitor, K⁺ efflux inhibitor |
| Methotrexate | DNA, RNA synthesis inhibitor |
| Bruton's tyrosine kinase (BTK) Inhibitor(s): ibrutinib (IMBRUVICA ®) | Bruton's tyrosine kinase; caspase-1 inhibitor |
| Sβ-485232 (GSK) | IL-18 inhibitor |
| β-hydroxybutyrate | NLRP3 inflammasome inhibitor |
| Interferon α | NLRP3 inflammasome inhibitor |
| Interferon β (BETASERON ®) | NLRP3 inflammasome inhibitor |
| Resveratrol | Autophagy inducer |
| Arglabin | Autophagy inducer |
| CB2R agonist (HU-308 Tocris Bioscience) | Autophagy inducer |
| VX-765 | Caspase-1 inhibitor |
| Ac-YVAD-cmk | Caspase-1 inhibitor |
| Bafilomycin A1 | Late phase autophagy inhibitor |
| Isoliquiritigenin | NLRP3 inflammasome inhibitor |
| MCC950 | NLRP3 inflammasome inhibitor |
| Parthenolide | Caspase-1 and inflammasome inhibitor |

TABLE 2-continued

Inflammasome Inhibitors

| Inhibitor | Activity |
|---|---|
| Pepinh-MYD | Caspase-1 inhibitor |
| Bay 11-7082 NLRP3 | Inflammasome Inhibitor: IκB-α inhibitor |

TABLE 2-continued

Inflammasome Inhibitors

| Inhibitor | Activity |
|---|---|
| Z-VAD-FMK | Pan-caspase inhibitor; NLRP3 inflammasome inhibitor |

One embodiment described herein, is a pharmaceutical composition comprising 1 ng to 10,000 mg of each of one or more anti-cytokine antibodies, anti-receptor antibodies, soluble receptors, receptor inhibitors, or blocking agents. In one aspect, the composition comprises about 1 ng, about 10 ng, about 50 ng, about 100 ng, about 500 ng, about 1 μg, about 10 μg, about 50 μg, about 100 μg, about 500 μg, about 1 mg, about 2 mg, about 5 mg, about 10 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, about 1000 mg, about 2000 mg, about 3000 mg, about 4000 mg, about 5000 mg, about 6000 mg, about 7000 mg, about 8000 mg, about 9000 mg, about 10000 mg, or even greater amounts for each of the one or more anti-cytokine antibodies, anti-receptor antibodies, soluble receptors, receptor inhibitors, or blocking agents. With regard to inflammasome inhibitors or blocking agents, the majority of these agents are small molecules and thus the therapeutic amounts are much less than biologic agents.

Another embodiment described herein, is a pharmaceutical composition wherein the administration comprises one or more anti-cytokine antibodies, anti-receptor antibodies, soluble receptors, receptor inhibitors, or blocking agents comprising about 0.01 mg/kg, about 0.05 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, about 40 mg/kg, about 50 mg/kg, about 60 mg/kg, about 70 mg/kg, about 80 mg/kg, about 90 mg/kg, about 100 mg/kg, about 120 mg/kg, about 150 mg/kg, about 175 mg/kg, about 200 mg/kg, about 250 mg/kg, about 300 mg/kg, about 400 mg/kg, about 500 mg/kg, or even greater for each of the one or more anti-cytokine antibodies, anti-receptor antibodies, soluble receptors, receptor inhibitors, or blocking agents.

Another embodiment described herein, is a pharmaceutical composition comprising one or more anti-cytokine antibodies, anti-receptor antibodies, soluble receptors, receptor inhibitors, or blocking agents each having a concentration of about 0.1 mg/mL, about 0.2 mg/mL, about 0.5 mg/mL, about 1 mg/mL, about 2 mg/mL, about 5 mg/mL, about 10 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 500 mg/mL, or even greater for each of the one or more anti-cytokine antibodies, anti-receptor antibodies, soluble receptors, receptor inhibitors, or blocking agents.

Another embodiment described herein is a pharmaceutical composition comprising one or more anti-cytokine antibodies, anti-receptor antibodies, soluble receptors, receptor inhibitors, or blocking agents (particularly any from Tables 1 and 2), comprising each protein at the indicated dose. In one aspect, the amount of each protein in the composition is independently increased between 1.5-fold to 50-fold of the indicated dose, including each integer within the specified range. In another aspect, the amount of each protein in the composition is independently increased about 1.5 fold; about 2-fold, about 3-fold, about 4-fold; about 5-fold, about 6-fold; about 7-fold; about 8-fold, about 10-fold, about 20-fold, about 50-fold, or about 100-fold of the indicated dose.

The frequency of dosing will depend upon the pharmacokinetic parameters of the therapeutic agent being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The phrases and terms "can be administered by injection," "injectable," or "injectability" refer to a combination of factors such as a certain force applied to a plunger of a syringe containing the anti-cytokine antibodies, anti-receptor antibodies, soluble receptors, receptor inhibitors, or blocking agents described herein dissolved in a liquid at a certain concentration (w/v) and at a certain temperature, a needle of a given inner diameter connected to the outlet of such syringe, and the time required to extrude a certain volume of the anti-cytokine antibodies, anti-receptor antibodies, soluble receptors, receptor inhibitors, or blocking agents from the syringe through the needle.

In one embodiment, an injectability measurement is carried out for the anti-cytokine antibodies, anti-receptor antibodies, soluble receptors, receptor inhibitors, or blocking agents suspended in PBS or physiological saline to a concentration of about 0.1% to about 20% (w/v) including all integers within the specified percentage range.

Another embodiment described herein is a pharmaceutical composition of the anti-cytokine antibodies, anti-receptor antibodies, soluble receptors, receptor inhibitors, or blocking agents described herein. The pharmaceutical compositions can comprise one or more excipients, such as:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability.

(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum.

(iii) Preservatives and/or antimicrobials: multidose parenteral preparations may require the addition of preservatives at a sufficient concentration to minimize the risk of subjects becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride.

(iv) Stabilizers: Stabilization is achieved by strengthening of the protein-stabilising forces, by destabilization of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, polyethylene glycol, polyvinylpyrrolidone, protamine, or human serum albumin may be used.

(v) Anti-adsorption agents: Mainly ionic or ion-ionic surfactants or other proteins or soluble polymers are used to coat or adsorb competitively to the inner surface of the composition's container, e.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically, a monolayer of surfactant is formed at the interface just above the CMC value.

(vi) Lyophilization or cryoprotectants: During freeze- or spray drying, excipients may counteract the destabilising effects caused by hydrogen bond breaking and water removal. For this purpose, sugars and polyols may be used, but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol or sucrose are known to enhance physical stability of a lyophilized cake. Mannitol may also be combined with trehalose. Trehalose may also be combined with sorbitol or sorbitol may be used as the sole protectant. Starch or starch derivatives may also be used.

(vii) Oxidation protection agents: antioxidants such as ascorbic acid, ectoine, methionine, glutathione, monothioglycerol, morin, polyethylenimine (PEI), propyl gallate, vitamin E, chelating agents such aus citric acid, EDTA, hexaphosphate, thioglycolic acid.

(viii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satiagum UTC 30, aliphatic poly(hydroxy acids), such as poly (D,L- or L-lactic acid) (PLA) and poly(glycolic acid) (PGA) and their copolymers (PLGA), terpolymers of D,L-lactide, glycolide and caprolactone, poloxamers, hydrophilic poly (oxyethylene) blocks and hydrophobic poly(oxypropylene) blocks to make up a triblock of poly(oxyethylene)-poly(oxypropylene)-poly(oxyethylene) (e.g., Pluronic™), polyetherester copolymer, such as a polyethylene glycol terephthalate/polybutylene terephthalate copolymer, sucrose acetate isobutyrate (SAM), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone. Such block copolymers as well as the above-mentioned poloxamers may exhibit reverse thermal gelation behavior (fluid state at room temperature to facilitate administration and gel state above sol-gel transition temperature at body temperature after injection).

(ix) Diffusion agents: modifies the permeability of connective tissue through the hydrolysis of components of the extracellular matrix in the interstitial space such as, but not limited to, hyaluronic acid, a polysaccharide found in the intercellular space of connective tissue. A spreading agent such as, but not limited to, hyaluronidase temporarily decreases the viscosity of the extracellular matrix and promotes diffusion of injected drugs.

(x) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture.

In one embodiment, the anti-cytokine antibodies, anti-receptor antibodies, soluble receptors, receptor inhibitors, or blocking agents are sufficiently dosed in the composition to provide therapeutically effective amounts of biologically active agent for at least 12 hours in one application. In one aspect, one application of anti-cytokine antibodies, anti-receptor antibodies, soluble receptors, receptor inhibitors, or blocking agents is sufficient for about 0.5 day, 1 day, about 2 days, about 3 days, about 4 days, about 5 days, about 6 days, about 7 days, about 1 week, about 2 weeks, about 3 weeks, about 4 weeks, one month, 2 months, 3 months, 4 months, 6 months, 9 months, one year, 2 years, 3 years, 4 years, or even longer.

In one embodiment, the anti-cytokine antibodies, anti-receptor antibodies, soluble receptors, receptor inhibitors, or blocking agents are provided as a single dose, meaning that the container in which it is supplied contains one pharmaceutical dose.

In another embodiment, the composition is provided as a multiple dose composition, meaning that it contains more than one therapeutic dose. Preferably, a multiple dose composition contains at least 2 doses. Such multiple dose compositions can be used for different subjects in need thereof or for use in one subject, wherein the remaining doses are stored until needed after the administration of the first dose.

In another embodiment, the anti-cytokine antibodies, anti-receptor antibodies, soluble receptors, receptor inhibitors, or blocking agents are provided in one or more containers. For liquid or suspension compositions, the container is preferably a single chamber syringe. For dry compositions, preferably the container is a dual-chamber syringe. The dry composition is provided in a first chamber of the dual-chamber syringe and reconstitution solution is provided in a second chamber of the dual-chamber syringe.

Prior to administering a dry or lyophilized composition of anti-cytokine antibodies, anti-receptor antibodies, soluble receptors, receptor inhibitors, or blocking agents to a subject in need thereof, the dry composition is reconstituted. Reconstitution can take place in the container in which the dry composition is provided, such as in a vial, syringe, dual-chamber syringe, ampoule, and cartridge. Reconstitution is done by adding a predefined amount of reconstitution solution to the dry composition. Reconstitution solutions are sterile liquids, such as phosphate buffered saline, isotonic saline, water for injection, or other buffers, which may contain further excipients, such as preservatives and/or antimicrobials, such as, for example, benzylalcohol and cresol. Preferably, the reconstitution solution is sterile water for injection. Alternatively, the reconstitution solution is physiological saline or sterile phosphate buffered saline (PBS).

Another embodiment is a method of preparing a reconstituted composition comprising a therapeutically effective amount of anti-cytokine antibodies, anti-receptor antibodies, soluble receptors, receptor inhibitors, or blocking agents, and optionally one or more pharmaceutically acceptable excipients, the method comprising the step of contacting the composition with a volume of reconstitution vehicle. The reconstituted anti-cytokine antibodies, anti-receptor antibodies, soluble receptors, receptor inhibitors, or blocking agents may then be administered by injection or other routes.

Another embodiment is a reconstituted composition comprising a therapeutically effective amount of anti-cytokine antibodies, anti-receptor antibodies, soluble receptors, receptor inhibitors, or blocking agents, a reconstitution vehicle, and optionally one or more pharmaceutically acceptable excipients.

Another embodiment is a pre-filled syringe comprising a solution or a suspension comprising a therapeutically effective amount of anti-cytokine antibodies, anti-receptor antibodies, soluble receptors, receptor inhibitors, or blocking agents, and optionally one or more pharmaceutically acceptable excipients. In one aspect, the syringe is filled with between about 0.01 mL and about 50 mL of anti-cytokine antibodies, anti-receptor antibodies, soluble receptors, receptor inhibitors, or blocking agents as described herein. In one aspect, the syringe is filled with between about 0.05 mL and about 50 mL, between about 1 mL and about 20 mL, between about 1 mL and about 10 mL, between about 1 mL and about 5 mL, or about 0.5 to about 5 mL. In one embodiment, the syringe is filled with 0.5 mL to about 2 mL of anti-cytokine antibodies, anti-receptor antibodies, soluble receptors, receptor inhibitors, or blocking agents as described herein. In some aspects, a syringe is filled with about 0.1 mL, about 0.2 mL, about 0.3 mL, about 0.4 mL, 0.5 mL, about 0.6 mL, about 0.7 mL, about 0.8 mL, about 0.9 mL, about 1 mL, about 1.2 mL, about 1.5 mL, about 1.75 mL, about 2 mL, about 3 mL, about 4 mL, about 5 mL, about 7.5 mL, about 10 mL, about 15 mL, about 20 mL, about 25 mL, about 30 mL, about 40 mL, about 50 mL, or greater than 50 mL of anti-cytokine antibodies, anti-receptor antibodies, soluble receptors, receptor inhibitors, or blocking agents as described herein. A syringe is often filled with more than the desired dose to be administered to the patient, to take into account wastage due to "dead space" within the syringe and needle. There may also be a pre-determined amount of waste when the syringe is primed by the physician, so that it is ready to inject the patient.

In one embodiment, a syringe is filled with a dosage volume (i.e., the volume of medicament intended for delivery to the patent) of between about 0.01 mL and about 5 mL depending on the route of injection (e.g., between about 0.01 mL and about 0.1 mL, between about 0.1 mL and about 0.5 mL, between about 0.2 mL and about 2 mL, between about 0.5 mL and about 5 mL, or between about 1 mL and about 5 mL) of about 0.6 mL, about 0.7 mL, about 0.8 mL, about 0.9 mL, about 1 mL, about 1.2 mL, about 1.5 mL, about 1.75 mL, about 2 mL, as described herein. In one embodiment intended for subcutaneous injection, a syringe is filled with a dosage volume of between about 0.1 mL and about 5.0 mL of anti-cytokine antibodies, anti-receptor antibodies, soluble receptors, receptor inhibitors, or blocking agents with concentration(s) of 0.1 mg/mL to 500 mg/mL as described herein. In other embodiments intended for injection by other routes, a syringe is filled with a dosage volume of between about 0.01 mL and about 5.0 mL of anti-cytokine antibodies, anti-receptor antibodies, soluble receptors, receptor inhibitors, or blocking agents with a drug concentration of 0.1 mg/mL to 200 mg/mL as described herein. In some aspects, a syringe is filled with about 0.01 mL, about 0.02 mL, about 0.03 mL, about 0.04 mL, about 0.05 mL, about 0.06 mL, about 0.07 mL, about 0.08 mL, about 0.09 mL, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.2 mL, about 1.5 mL, about 1.75 mL, about 2 mL, about 2.5 mL, about 3 mL, about 4 mL, or about 5 mL of anti-cytokine antibodies, anti-receptor antibodies, soluble receptors, receptor inhibitors, or blocking agents as described herein for delivery to a patient in need thereof.

As the syringe contains a medicament solution, the outlet may be reversibly sealed to maintain sterility of the medicament. This sealing may be achieved by a sealing device as is known in the art, such as a luer lock or a tamper resistant seal.

Another embodiment is a kit comprising one or more pre-filled syringes comprising a solution or suspension of one or more anti-cytokine antibodies, anti-receptor antibodies, soluble receptors, receptor inhibitors, or blocking agents as described herein. In one embodiment, such a kit comprises a pre-filled syringe comprising anti-cytokine antibodies, anti-receptor antibodies, soluble receptors, receptor inhibitors, or blocking agents as described herein in a blister pack or a sealed sleeve. The blister pack or sleeve may be sterile on the inside. In one aspect, pre-filled syringes as described herein may be placed inside such blister packs or sleeves prior to undergoing sterilization, for example terminal sterilization.

Such a kit may further comprise one or more needles for administration of anti-cytokine antibodies, anti-receptor antibodies, soluble receptors, receptor inhibitors, or blocking agents as described herein. Such kits may further comprise instructions for use, a drug label, contraindications, warnings, or other relevant information. One embodiment described herein is a carton or package comprising one or more pre-filled syringes comprising one or more anti-cytokine antibodies, anti-receptor antibodies, soluble receptors, receptor inhibitors, or blocking agents as described herein contained within a blister pack, a needle, and optionally instructions for administration, a drug label, contraindications, warnings, or other relevant information.

A terminal sterilization process may be used to sterilize the syringe and such a process may use a known process such as an ethylene oxide or a hydrogen peroxide ($H_2O_2$) sterilization process. Needles to be used with the syringe may be sterilised by the same methods as kits described herein. In one aspect, a package is exposed to the sterilising gas until the outside of the syringe is sterile. Following such a process, the outer surface of the syringe may remain sterile (whilst in its blister pack) for up to 6 months, 9 months, 12 months, 15 months, 18 months, 24 months or longer. Thus, in one embodiment, a pre-filed syringe as described herein (in its blister pack) may have a shelf life of up to 6 months, 9 months, 12 months, 15 months, 18 months, 24 months or even longer. In one embodiment, less than one syringe in a million has detectable microbial presence on the outside of the syringe after 18 months of storage. In one aspect, the pre-filled syringe has been sterilised using ethylene oxide with a Sterility Assurance Level of at least $10^{-6}$. In another aspect, the pre-filled syringe has been sterilised using hydrogen peroxide with a Sterility Assurance Level of at least $10^{-6}$. Significant amounts of the sterilising gas should not enter the variable volume chamber of the syringe. The term "significant amounts" As used herein, refers to an amount of gas that would cause unacceptable modification of the solution or suspension of anti-cytokine antibodies, anti-receptor antibodies, soluble receptors, receptor inhibitors, or blocking agents within the variable volume chamber. In one embodiment, the sterilization process causes ≤10% (preferably ≤5%, ≤3%, ≤1%) alkylation of the anti-cytokine antibodies, anti-receptor antibodies, soluble receptors, receptor inhibitors, or blocking agents. In one embodiment, the pre-filled syringe has been sterilised using ethylene oxide, but the outer surface of the syringe has ≤1 ppm, preferably ≤0.2 ppm ethylene oxide residue. In one embodiment, the pre-filled syringe has been sterilised using hydrogen peroxide, but the outer surface of the syringe has ≤1 ppm, preferably ≤0.2 ppm hydrogen peroxide residue. In another embodiment, the pre-filled syringe has been sterilised using ethylene oxide, and the total ethylene oxide residue found on the outside of the syringe and inside of the blister pack is ≤0.1 mg. In another embodiment, the pre-filled syringe has been sterilised using hydrogen peroxide, and the total hydrogen peroxide residue found on the outside of the syringe and inside of the blister pack is ≤0.1 mg.

Another aspect is a kit of parts. For liquid and suspension compositions, and when the administration device is simply a hypodermic syringe, the kit may comprise a syringe, a needle, and a container comprising the anti-cytokine antibodies and soluble receptors for use with the syringe. In case of a dry composition, the container may have one chamber containing the dry composition of anti-cytokine antibodies, anti-receptor antibodies, soluble receptors, receptor inhibitors, or blocking agents, and a second chamber comprising a reconstitution solution. In one embodiment, the injection device is a hypodermic syringe adapted so the separate container with the anti-cytokine antibodies and soluble receptors can engage with the injection device such that in use the liquid, suspension, or reconstituted dry composition in the container is in fluid connection with the outlet of the injection device. Examples of administration devices include but are not limited to hypodermic syringes and pen injector devices. Particularly preferred injection devices are the pen injectors, in which case the container is a cartridge, preferably a disposable cartridge.

Another embodiment comprises a kit comprising a needle and a container containing the anti-cytokine antibodies, anti-receptor antibodies, soluble receptors, receptor inhibitors, or blocking agents and optionally further containing a reconstitution solution, the container being adapted for use with the needle. In one aspect, the container is a pre-filled syringe. In another aspect, the container is dual chambered syringe.

Another embodiment is a cartridge containing a composition of anti-cytokine antibodies, anti-receptor antibodies, soluble receptors, receptor inhibitors, or blocking agents as described herein for use with a pen injector device. The cartridge may contain a single dose or plurality of doses of anti-cytokine antibodies, anti-receptor antibodies, soluble receptors, receptor inhibitors, or blocking agents.

It will be apparent to one of ordinary skill in the relevant art that suitable modifications and adaptations to the compositions, formulations, methods, processes, and applications described herein can be made without departing from the scope of any embodiments or aspects thereof. The compositions, methods, and experiments provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

EXAMPLES

Example 1

Animal Research

Female 10-12 week old C57BL/6 and Caspase-1−/− (C57BL/6 background) mice were obtained from The Jackson Laboratory (Bar Harbor, Me.) and NLRP3−/− (C57BL/6 background) were obtained from University of Lausanne (Switzerland). Mice were provided a standard laboratory diet and water, and maintained under pathogen-free conditions under a 12-hour light/dark cycle. All experiments were carried out under the guidelines of the Institutional Animal Care and Use Committee (IACUC) at Rush University Medical Center. The protocol was approved by the committee on the Ethics of Animal Experiments of Rush University Medical Center and all experiments in this study were conducted adhering to the institution's guidelines for animal husbandry, and followed the guidelines and basic principals in the Public Health Service Policy on Humane Care and Use of Laboratory Animals, and the Guide for the Care and Use of Laboratory Animals, United States Institute of Laboratory Animal Resources, National Research Council. All efforts were made to minimize suffering; all manipulations were performed under isoflurane and mice were sacrificed by cervical dislocation after being administrated isoflurane.

Media and Reagents

Isolated murine and human cells were cultured with sterile RPMI 1640 supplemented with L-glutamine, penicillin, streptomycin, 25 mM HEPES, pH 7.4 (Lonza, Walkersville, Md.).

Nickel (II) chloride ($NiCl_2$), cobalt (II) chloride ($CoCl_2$), phorbol 12-myristate 13-acetate (PMA), ionomycin, phytohemagglutinin (PHA), and Mitomycin-C were purchased from Sigma Aldrich (St. Louis, Mo.). $NiCl_2$ and $CoCl_2$ were reconstituted in sterile water and stock solutions were freshly prepared for each in vitro and in vivo experiment. Complete Freund's Adjuvant (CFA) was purchased from InvivoGen (San Diego, Calif.).

In Vivo Delayed Type Hypersensitivity (DTH) to Orthopedic Implant Metal(s)

DTH responses comprise two phases: (1) sensitization and (2) effector phase. (1) Sensitization phase to implant metal(s): To induce DTH with orthopedic implant metal(s), mice were injected with 125 µL intraperitoneally (i.p) on day 1 and day 10, with either an emulsion of the adjuvant CFA with sterile 1×PBS (137 mM NaCl, 2.7 mM KCl, 10 mM $Na_2HPO_4$, $KH_2PO_4$, pH. 7.4) at equal volumes (control group) or an emulsion of CFA with soluble 10 mM stock concentration of $NiCl_2$ and $CoCl_2$ (metal-sensitized group) for initial metal sensitization (previously shown that $NiCl_2$ is most effective sensitizer at this concentration). Ashrin et al., J. Immunol. 192(9):4025-4031 (2014); Sato et al., Clin. Exp. Allergy 37(5):743-751 (2007). Intraperitoneal injections did not cause any keloid lesions at the injection site. (2) Effector phase to implant metal(s): Re-exposure to the metal allergen leads to DTH reaction during the effector phase. Therefore, on day 12, a 50 µL mixture of either sterile 1×PBS (control group) or $NiCl_2$ (metal-sensitized group) with an equivalent volume of CFA was injected subcutaneously on top of the right paw. DTH was determined 48 h post re-exposure to metal allergen (day 14) by measuring changes in paw inflammation using a digital caliber (blinded assessment) and the induced difference was recorded. Each group consisted of 3-5 mice and experiments were performed at least three independent times.

Histology

Murine paws were fixed with 10% phosphate buffered formaldehyde. Paraffin-embedded tissue anterior-posterior (AP) plane 5 µm sections were stained with hemotoxylin and eosin using standard techniques.

Lymphocyte Transformation Test (LTT) Assay for Determination of In Vitro Metal Reactivity In addition to determination of paw swelling after recall with $NiCl_2$, proliferation in vitro of lymphocytes was measured. Spleens were obtained aseptically 48 h after challenge and splenic effector CD4+ T cells were isolated using negative selection kit following manufacturer's protocol (EasySep Mouse CD4+ T cell isolation kit; $2.5 \times 10^5$ cells/per well in 96 well flat bottom plates). Splenic CD4+ T cells were co-incubated with syngeneic mitomycin-C treated naïve splenic ($2.5 \times 10^5$ cells/per well) antigen-presenting cells (APCs) with or without 0.0001 mM or 0.001 mM of soluble metal ions $NiCl_2$ or $CoCl_2$, and 0.01 mg/mL phytohemagglutinin (PHA) as a positive control, in RPMI 1640 media containing 10% fetal bovine serum (FBS; Hyclone Laboratories, Inc.) at 37° C. and 0.5% $CO_2$ for 4 days. Syngeneic naïve spleen APCs were incubated at $5 \times 10^6$ cells/mL with 25 µg/mL of mitomycin-C for 30 minutes to inactivate proliferation. At day 3 of cell culture, $^3$H-thymidine was added. At day 4, T-cell proliferation was assessed via $^3$H-thymidine incorporation that was determined using a beta scintillation counter.

Human Lymphocyte Isolation

De-identified human peripheral blood mononuclear cells were isolated from 30 mL of peripheral blood using density gradient separation (Ficoll-isopaque, Pharmacia, Piscataway, N.J.). Ficoll gradient separated mononuclear cells are generally comprised of 85-95% lymphocytes with 5-13% monocytes and <0.1% dendritic cells with limited contamination (i.e., <5% erythrocytes and <3% granulocytes). Collected PBMCs (white buffy coat) were washed in sterile 1×PBS and resuspended in RPMI-1640 medium with 10% autologous serum and cultured with either no metal (plain media) as a negative control, PHA as a positive control, or with soluble nickel ($NiCl_2$) or cobalt ($CoCl_2$) at 37° C. and 0.5% $CO_2$ for 6 days. At day 5 of cell culture, $^3$H-thymidine was added. At day 6, T-cell proliferation was assessed via $^3$H-thymidine incorporation that was determined using a beta scintillation counter.

Anti-Mouse-IL-1R Local Treatment

Anti-mouse IL-1R1: A set of metal-sensitized C57BL/6 female mice received local paw administration on day 12 with 200 µg of anti-mouse IL-1R1 (for local in vivo blocking of IL-1R during the effector phase of metal-DTH responses) (clone JAMA-147; BioLegend, San Diego, Calif.) in concert with $NiCl_2$ and CFA. Rogers et al., Proc. Natl. Acad. Sci. USA 89(3):1011-1015 (1992); Rogers et al., J. Immunol. 153(5):2093-2101 (1994).

Anti-Mouse-CD86 Treatment

Anti-mouse CD86 MAb treatment: Mice were treated with 400 µg of InVivoMAb anti-mouse CD86 (B7-2; BioXCell, West Lebanon, N.H.) in 200 µL 1×PBS starting at day 1 of metal sensitization and subsequently received 200 µg of anti-mouse CD86 in 1×PBS after 48 hours and every 48 hours until the experiment was terminated on day 14. Marshall et al., J. Immunol. 193(11):5525-5533 (2014); Moser et al., PLoS Pathog. 10(8):e1004315 (2014).

Anti-Mouse-IL-17A Monoclonal Antibody Treatment

Mice were treated with 400 µg of InVivoMAb anti-mouse IL-17A (BioXCell, West Lebanon, N.H.) in 200 µL 1×PBS starting at day 1 of metal sensitization and subsequently received 200 µg of anti-mouse IL-17A in 1×PBS after 48 hours and every 48 hours until the experiment was terminated on day 14. Atkinson et al., Dis. Model. Mech. 9(4):427-440 (2016).

In Vitro Treatment of Human Lymphocytes with Inflammasome and IL-17A Inhibitor(s)

Inflammasome Inhibitor(s)

Isolated human PBMCs were co-incubated in vitro with either MCC950, a NLRP3 inflammasome inhibitor (InvivoGen), Caspase-1 inhibitor (Caspase-1/ICE inhibitor Z-WEHD-FMK) or recombinant human IL-1Ra (R&D Systems. Inc., Minneapolis, Minn.) for metal-LTT assay or cytokine analysis according to manufacturer's protocol and working concentration. Caicedo et al., J. Biomed. Mater. Res. A 93(4):1312-1321 (2010).

IL-17A Monoclonal Antibody

Isolated human PBMCs were co-incubated in vitro with IL-17A monoclonal antibody (eBio64CAP17; ThermoFisher Scientific) for neutralization of IL-17A bioactivity for metal-lymphocyte transformation test assay or cytokine analysis according to the manufacturer's protocol and concentration.

Cytokine Analyses

Sandwich ELISAs for mouse IL-17A/F and IFN-γ (R&D Systems Inc., Minneapolis, Minn.) were used to detect cytokine production in both non-sensitized and metal-sensitized female mouse spleens and isolated CD4+ T-cells that were harvested 48 h post paw re-challenge to metal allergen (day 14). Supernatants from control and metal-challenged murine cells were collected after 4 days. Sandwich ELISAs for human IL-17A/F and IFN-γ (R&D Systems) were used to detect cytokine production in supernatants from isolated control and metal-challenged human PBMCs that were collected after 5 days. All samples for ELISA were performed in triplicate in 96 well plates and were stored at −80° C. until analysis, following manufacturer's protocol.

Statistical Analyses

D'Agostino and Pearson omnibus normality test was performed to determine normality for each of the data sets. If the data set passed the normality test ($\alpha=0.05$), then data was subsequently analyzed using Fisher's Least Significant Difference for comparison of groups post-hoc after significance was determined with ANOVA. Results are represented as the mean±SEM from triplicate data from three independent experiments. To determine statistical significant differences among intragroup comparisons, two-tailed paired Student's t-test were used and unpaired Student's t-test was used as appropriate for intergroup comparisons. The Mann-Whitney test was used for the comparison of two groups and the Kruskal-Wallis test for the comparison of more than two data sets for non-normal distributed data or n<15 data points. Kitchen, *Am. J. Ophthalmol.* 47(4): 571-572 (2009). All statistical analyses were performed using Prism 6.0 (GraphPad, San Diego, Calif.). Statistical difference was considered significant at $p \leq 0.05$.

Example 2

In Vivo Induction of DTH Responses to Orthopedic Metal Implant Debris

Figure 1B:
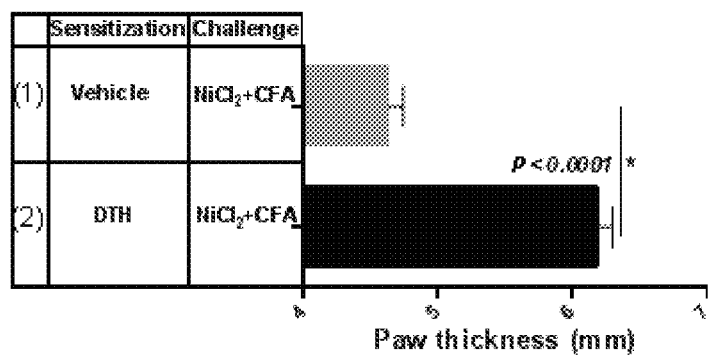
FIG. 1B. DTH was determined by measuring paw thickness 48 h after challenge (day 14) in C57BL/6 mice that were sensitized and challenged as indicated on day 12. Data represent three independent experiments with four mice/group in each experiment. The amount of cell proliferation is represented as the mean of counts per minute (cpm) ±SEM. Statistical significance was determined by Student's unpaired two-tailed t-test and asterisk (*) denote significant differences P≤0.05.
Figure 1C:
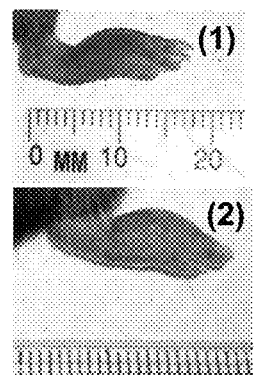
FIG. 1C. Representative photographs of inflammatory lesions in the paw of vehicle and metal-DTH mice on day 14. C57BL/6 mice that were paw challenged without prior sensitization, vehicle group (Group 1), served as negative controls. Photographs correspond to data shown in FIG. 1B.
Figure 1D:
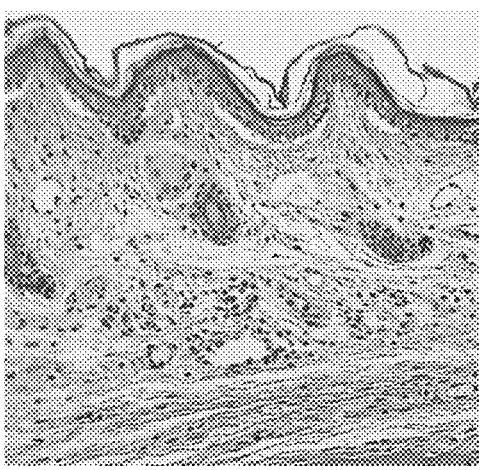
FIG. 1D. Representative paw histology sections from vehicle-treated C57BL/6 mice.
Figure 1E:
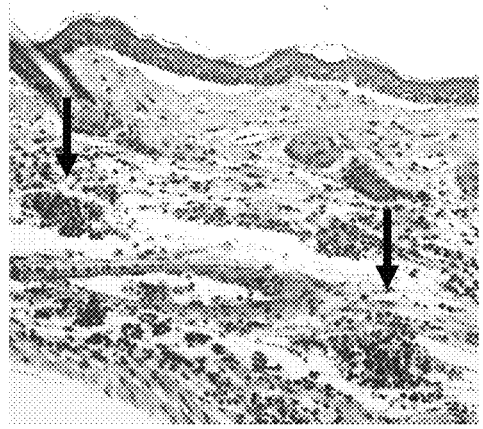
FIG. 1E. Representative paw histology sections from DTH-treated C57BL/6 mice.

Recent prospective studies have shown that the rate and degree of metal sensitization in patients with metal on metal hip arthroplasties is increased compared to the general population, supporting the postulate that metal-induced lymphocyte reactivity increases with increased metal exposure. Hallab et al., *J. Arthroplasty* 19(8 Suppl 3):88-93 (2004). To determine if in vivo exposure to clinically relevant implant metal degradation productions (i.e., metal ions) induces metal-DTH responses, female C57BL/6 mice were sensitized with an intraperitoneal (i.p.) injection of a mixture of Complete Freund's Adjuvant (CFA), $NiCl_2$, and $CoCl_2$ on day 1 and day 10 (FIG. 1A). Sato et al., *Clin. Exp. Allergy* 37(5):743-751 (2007). Subsequent re-exposure/challenge to metal allergen ($NiCl_2$) leads to a DTH reaction during the effector phase. To assess whether mice developed a DTH reaction to orthopedic metals, mice were challenged on day 12 by a subcutaneous injection into their paw superficially with $NiCl_2$ and CFA. Mice in the vehicle group that received paw challenge without prior metal sensitization served as negative controls. On day 14, metal-DTH responses were evaluated and measured by a blind assessment of localized paw inflammation via a digital caliber (FIG. 1B). Upon challenge with Ni, the sensitized-mice had a greater severity of a metal-DTH response as measured by significant increase in paw inflammation (6.195 mm mean paw inflammation; p<0.0001) as compared to vehicle group. Additionally, redness and swelling were only observed in the paw(s) of metal-sensitized C57BL/6 mice (FIGS. 1B and 1C). Histological examination revealed dramatic differences in the infiltration of lymphocytes in the paw tissues of sensitized mice (FIG. 1D vs. 1E). These results indicate that in vivo exposure to implant metal degradation products can lead to robust metal-DTH responses.

Figure 2A:
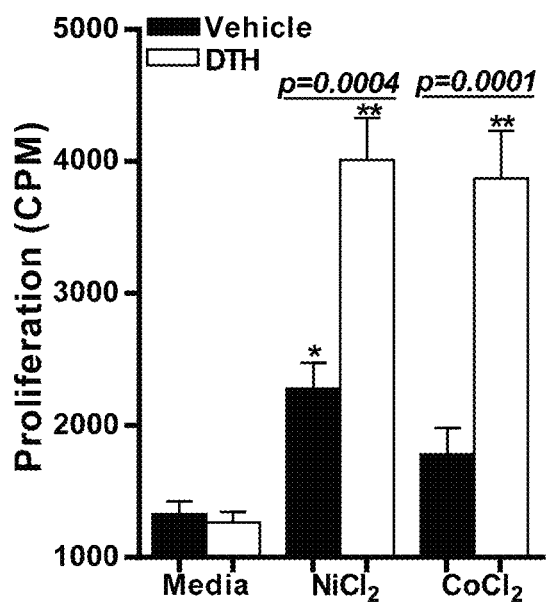
FIG. 2A. Metal-DTH responses to implant debris in metal-sensitized C57BL/6 mice induces metal-reactive CD4+ T cells. At day 14, spleens were harvested. CD4+ T cells were purified from mouse spleens and co-cultured with mitomycin-C treated naïve total spleen cells with or without Ni (0.001 mM) or Co (0.001 mM) challenge for 4 days. Proliferation of CD4+ T cells was measured by $^3$H-thymidine incorporation. Data represent one of three independent experiments with four mice/group in each experiment. Data are shown as mean±SEM. Statistical significance was determined by Student's unpaired two-tailed t-test and asterisk (*) denote significant differences P≤0.05.
Figure 2B:
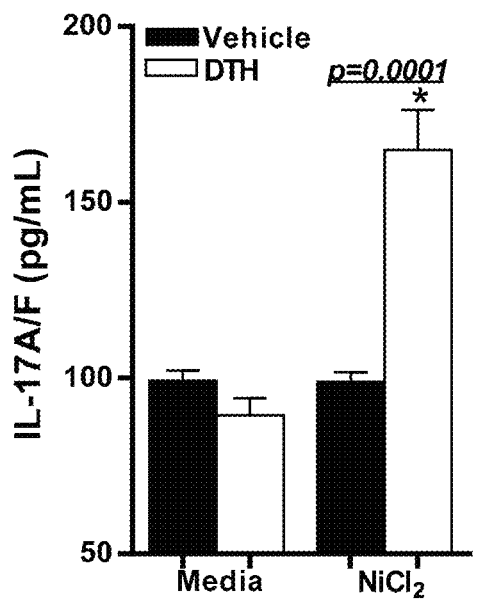
FIG. 2B. Supernatants were harvested and assayed by ELISA for IL-17A/F. Data represent one of three independent experiments with four mice/group in each experiment. Data are shown as mean±SEM. Statistical significance was determined by Student's unpaired two-tailed t-test and asterisk (*) denote significant differences P≤0.05.
Figure 2C:
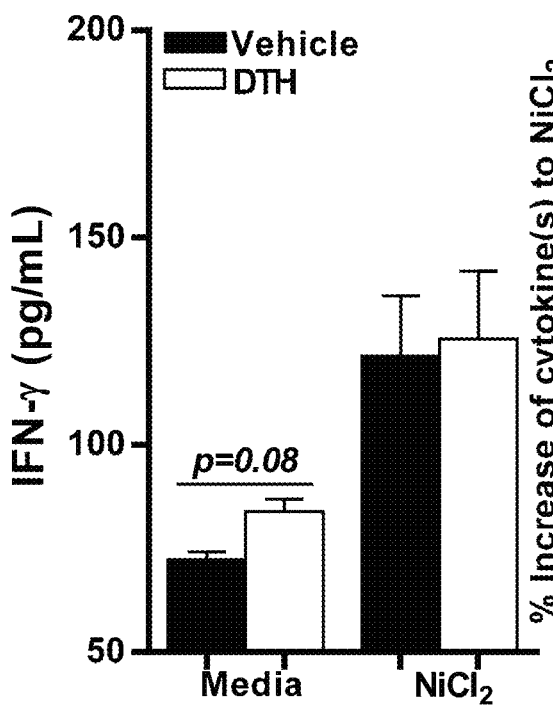
FIG. 2C. Supernatants were harvested and assayed by ELISA for IFN-γ. Data represent one of three independent experiments with four mice/group in each experiment. Data are shown as mean±SEM. Statistical significance was determined by Student's unpaired two-tailed t-test and asterisk (*) denote significant differences P≤0.05.
Figure 2D:
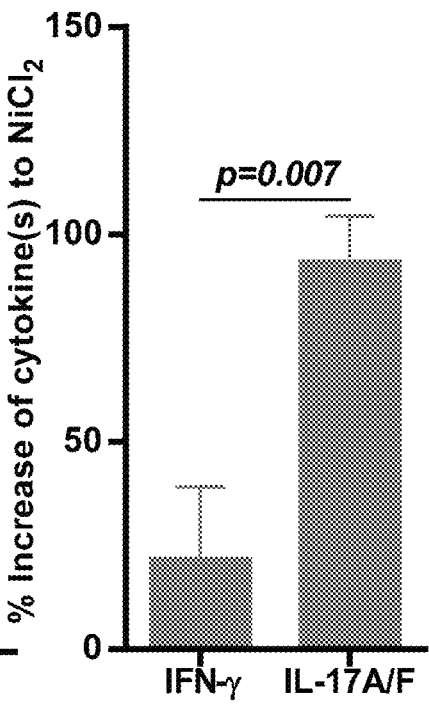
FIG. 2D. Percentage increase of produced cytokines in response to Ni challenge, calculated using cytokine production from FIGS. 1D and 1E from DTH vs. vehicle treated mice. Data represent one of three independent experiments with four mice/group in each experiment. Data are shown as mean±SEM. Statistical significance was determined by Student's unpaired two-tailed t-test and asterisk (*) denote significant differences P≤0.05.

In addition to determining paw swelling after re-exposure to $NiCl_2$, proliferation in vitro of splenic CD4+ T cells from vehicle and DTH mice was measured. CD4+ T cells from metal-DTH mice displayed a significant increase in $NiCl_2$ and $CoCl_2$ specific proliferation than CD4+ T cells from vehicle-treated mice (FIG. 2A). The proliferative response of CD4+ T cells from metal-DTH treated mice corresponded with a significant increase in IL-17A/F production in response to Ni (FIG. 2B). However, IFN-γ secretion by CD4+ T cells from metal-DTH treated mice was non-significantly increased in response to Ni (FIG. 2C). In contrast, CD4+ T cells from vehicle-treated mice did not exhibit any increase in IL-17A/F production but exhibited a non-significant increase in IFN-γ production in response to Ni (p=0.07; FIGS. 2B and 2C). These data demonstrate that metal-sensitized mice have a CD4+ T cell specificity recall response to Ni that is IL-17A/F mediated.

Example 3

Figure 3A:
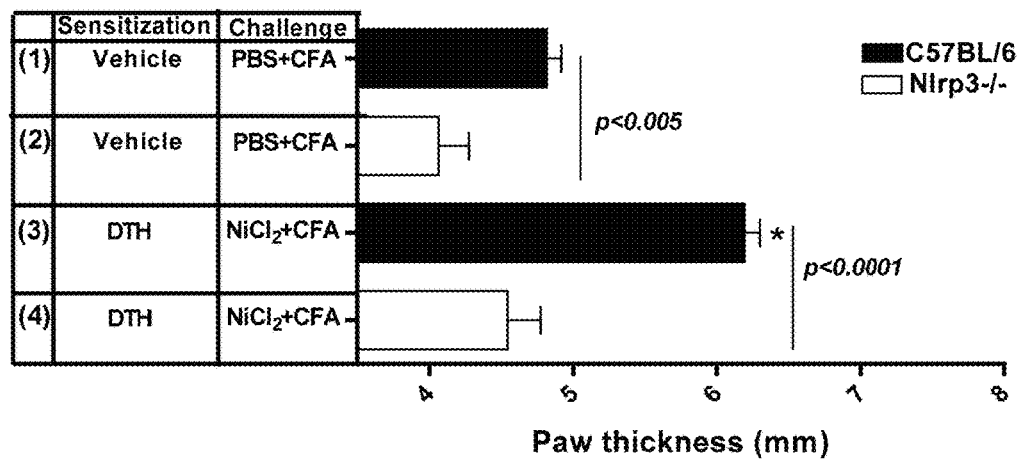
FIG. 3A. Nlrp3−/− mice do not exhibit metal-DTH reactivity in vivo or in vitro. DTH was determined by measuring paw thickness 48 h after challenge (day 14) in mice that were sensitized and challenged as indicated on day 12. Black bars correspond to vehicle- and metal-DTH treated C57BL/6 mice and white bars correspond to Nlrp3−/− mice.
Figure 3B:
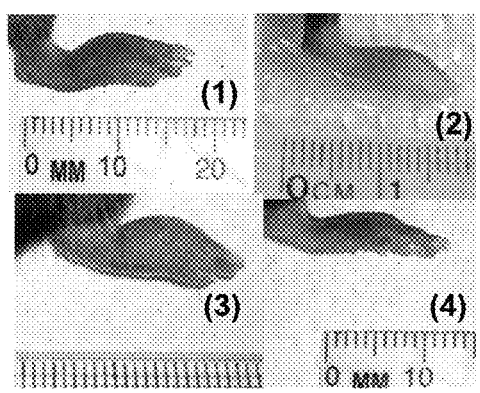
FIG. 3B. Corresponding representative photographs (corresponding to label group numbers 1-4 of FIG. 3A) of inflammatory lesions in the paw of vehicle- and metal-DTH treated C57BL/6 or Nlrp3−/− mice. At day 14, spleens were harvested co-cultured with or without Ni (0.001 mM) or Co (0.001 mM) challenge for 4 days.
Figure 3C:
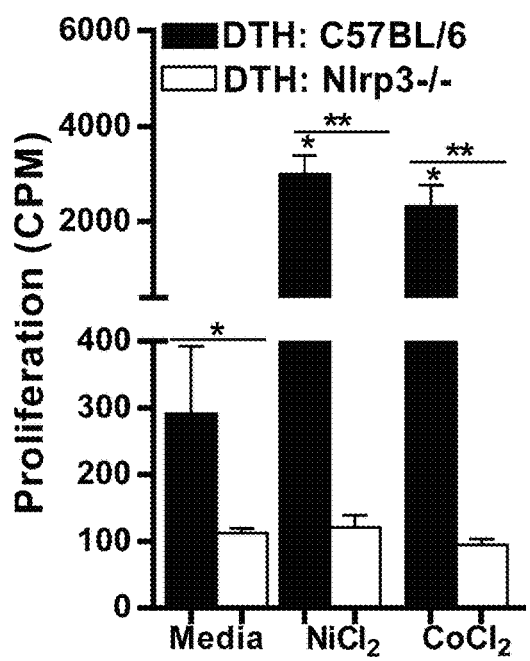
FIG. 3C. Proliferation of splenocytes was measured by $^3$H-thymidine incorporation. Data represent one of three independent experiments with 3-4 mice/group in each experiment. Data are shown as mean±SEM. Statistical significance was determined by Student's unpaired two-tailed t-test (*P≤0.05, **P≤0.001).

Inflammasome Activation is Required to Elicit a Metal-DTH Response in Sensitized Mice To evaluate the effect of NLRP3 inflammasome on metal-DTH responses, Nlrp3−/− mice were sensitized using this model system to induce metal-DTH responses (FIG. 1A). The mean paw thickness of both vehicle-treated and metal-sensitized-treated Nlrp3−/− mice was significantly decreased compared with that of vehicle and metal-DTH C57BL/6 mice (FIGS. 3A and 3B). Redness and swelling was not observed in the paw of Nlrp3−/− mice (FIG. 3B). Further, proliferation in vitro of isolated splenic cells from metal-DTH Nlrp3−/− mice displayed a significant decrease in $NiCl_2$ and $CoCl_2$ specific proliferation compared with metal-DTH C57BL/6 mice (FIG. 3C).

Figure 4A:
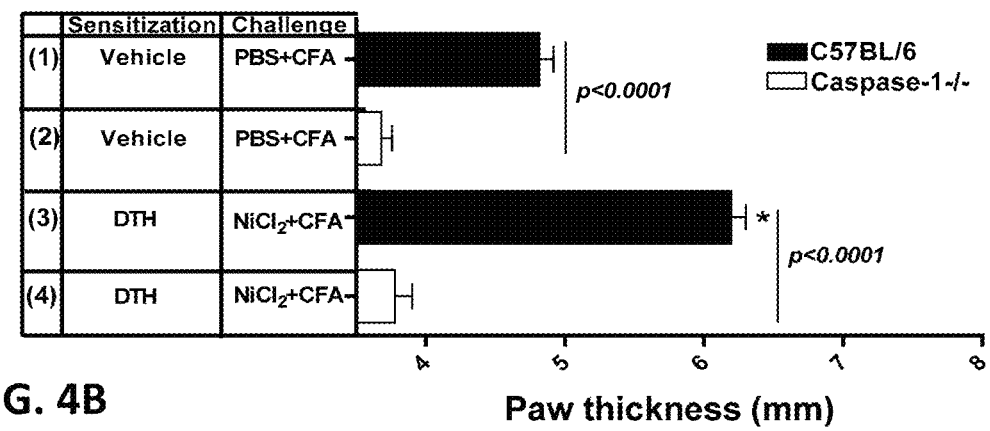
FIG. 4A. Caspase-1−/− mice do not exhibit metal-DTH reactivity in vivo or in vitro. DTH was determined by measuring paw thickness 48 h after challenge (day 14) in mice groups 1-4 that were sensitized and challenged as indicated on day 12.
Figure 4B:
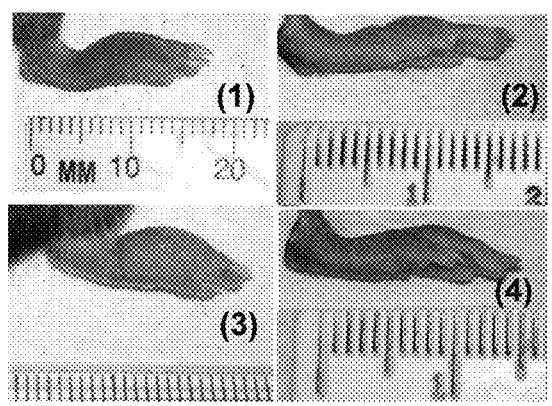
FIG. 4B. Corresponding representative photographs (corresponding to label group numbers 1-4 of FIG. 4A) of inflammatory lesions in the paw of vehicle- and metal-DTH treated C57BL/6 or Caspase-1−/− mice. At day 14, spleens were harvested co-cultured with or without Ni (0.001 mM) or Co (0.001 mM) challenge for 4 days.
Figure 4C:
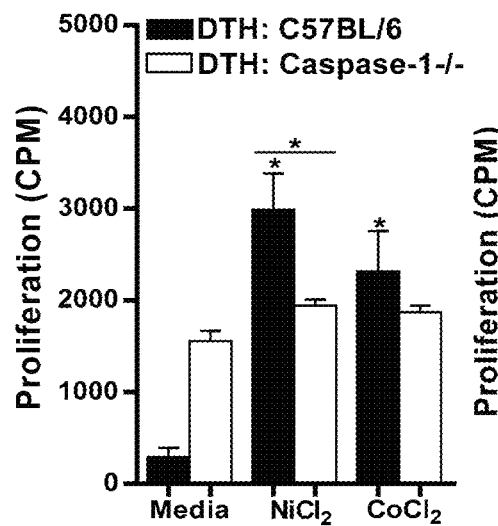
FIG. 4C. Proliferation of splenocytes was measured by $^3$H-thymidine incorporation. CD4+ T cells were purified from either DTH C57BL/6 or DTH Caspase-1−/− mouse spleens and co-cultured with mitomycin-C treated naïve total spleen cells from C57BL/6 or Caspase-1−/− mice respectively, with Ni (0.001 mM) challenge for 4 days.
Figure 4D:
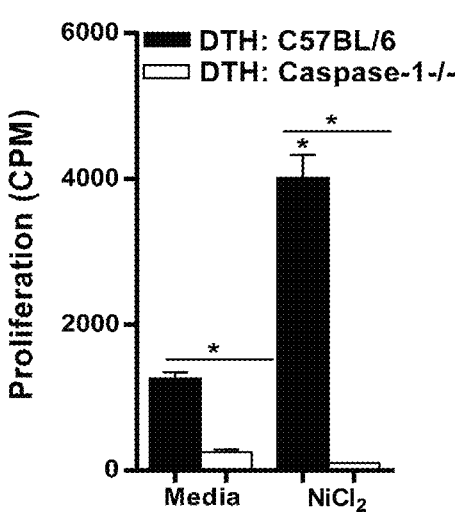
FIG. 4D. Proliferation of CD4+ T cells was measured by $^3$H-thymidine incorporation. Data represent one of three independent experiments with 3-4 mice/group in each experiment. Data are shown as mean±SEM. Statistical significance was determined by Student's unpaired two-tailed t-test (*P≤0.05).

NLRP3 inflammasome mediates the activation of caspase-1, which promotes the production of pro-inflammatory IL-1β. Thus, the rate-limiting step in inflammation due to IL-1β is the activation of caspase-1. To further assess the role of the inflammasome pathway, Caspase-1−/− mice were metal-sensitized. Metal-DTH Caspase-1−/− mice exhibited significantly less paw inflammation compared with C57BL/6 mice (FIGS. 4A and 4B). Further, metal-DTH Caspase-1−/− mice had less paw inflammation (mean paw thickness=3.77 mm) compared with metal-DTH Nlrp3−/− mice (mean paw thickness=4.54 mm; FIG. 3A vs. 4A). Caspase1−/− metal-DTH mice also displayed significant decreases in both splenic and CD4+ T cell proliferation to metal challenge (FIGS. 4C and 4D). These results reveal that metal-DTH responses to implant debris are dependent on active NLRP3 inflammasome and caspase-1 signaling in vivo and in vitro. These data also reveal that immune reactivity during a metal-DTH response is more dependent on active caspase-1 signaling than the NLRP3 inflammasome.

Example 4

Figure 5A:
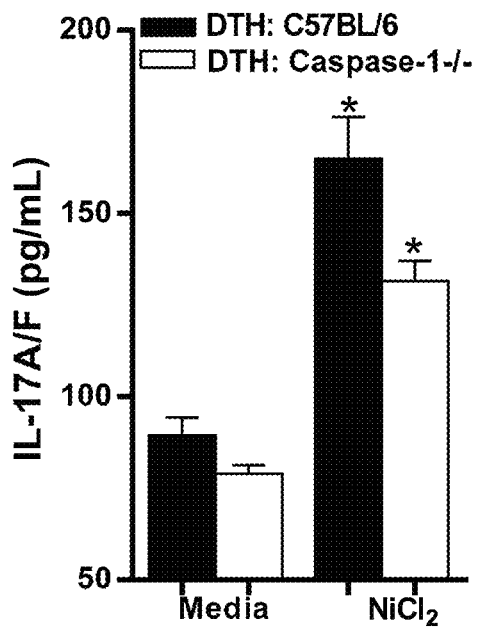
FIG. 5A. Cytokine production by CD4+ T cells from metal-DTH C57BL/6 and Caspase-1−/− mice. At day 14, spleens were harvested from metal-sensitized (DTH) C57BL/6 mice (black bars) and Caspase-1−/− mice (white bars). CD4+ T cells were purified from mouse spleens and co-cultured with mitomycin-C treated naïve total spleen cells from either C57BL/6 or Caspase-1 1−/− mice respectively, with or without Ni (0.001 mM) challenge for 4 days. Supernatants were harvested and assayed by ELISA for IL-17A/F. Data represent one of three independent experiments with four mice/group in each experiment. Data are shown as mean±SEM. Statistical significance was determined by Student's unpaired two-tailed t-test and asterisk (*) denote significant differences P≤0.05.
Figure 5B:
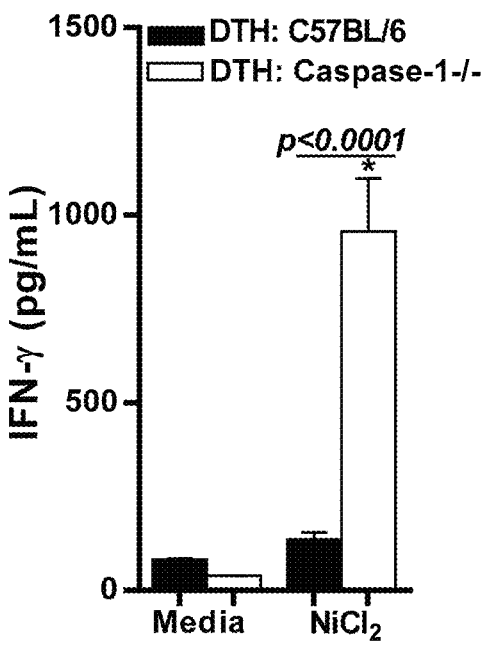
FIG. 5B. Supernatants were harvested and assayed by ELISA for IFN-γ. Data represent one of three independent experiments with four mice/group in each experiment. Data are shown as mean±SEM. Statistical significance was determined by Student's unpaired two-tailed t-test and asterisk (*) denote significant differences P≤0.05.

Metal-Sensitized Caspase-1−/− Deficient Mice Exhibit Robust Production of IFN-γ in Response to Nickel CD4+ T cells isolated from metal-sensitized Caspase-1−/− mice exhibited a significant increase of IL-17A/F expression in response to Ni (mean secretion=131.5 pg/mL; FIG. 5A). In addition, IFN-γ production by CD4+ T cells from metal-sensitized Caspase-1−/− mice was significantly increased in response to Ni (mean secretion=956.6 pg/mL), and compared to metal-sensitized C57BL/6 mice (p<0.0001; FIG. 5B). However, IFN-γ production was significantly greater than IL-17A/F production in metal-sensitized Caspase-1−/− mice in response to Ni (p=0.006) (compare data from FIG. 5A to 5B). The IL-17 secretion was likely suppressed due to the lack of inflammasome/caspase-1 signaling, and the ability of IFN-γ to suppress inflammatory IL-17 production. These data indicate that the absence of caspase-1 activity leads to the abatement of metal-DTH responses. This is likely due to significant increases in IFN-γ production that suppresses Ni-induced IL-17 production.

Example 5

Ni-Specific CD4+ T Cells Require Active Caspase-1

Figure 6:
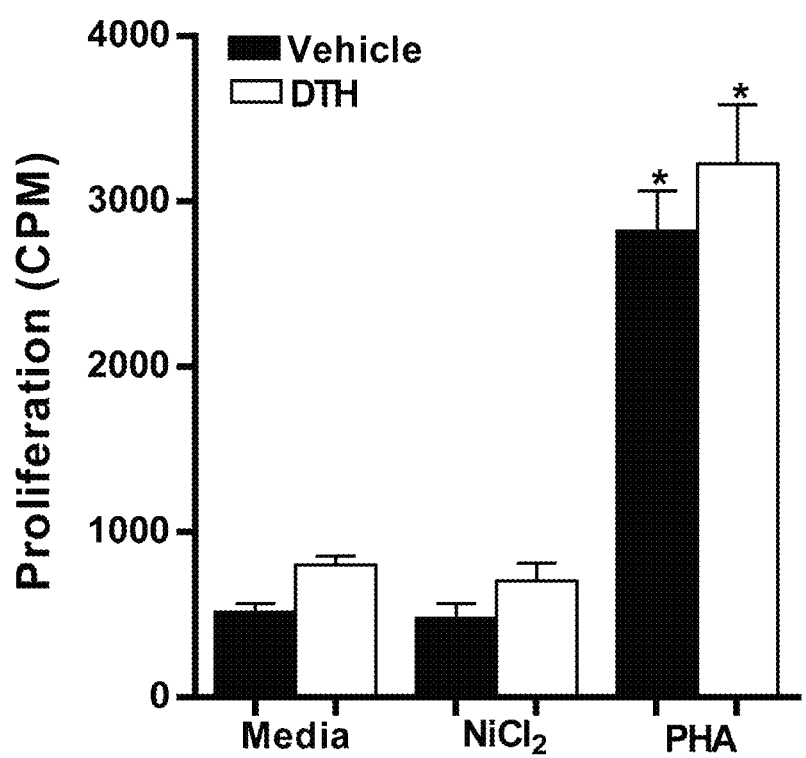
FIG. 6. Metal-reactive CD4+ T cells require caspase-1 activity by antigen presenting cells (APCs). At day 14, spleens were harvested from vehicle and metal-sensitized (DTH) C57BL/6 mice. CD4+ T cells were purified from mouse spleens and co-cultured with mitomycin-C treated naïve total spleen cells from Caspase-1−/− mice, with Ni (0.001 mM) challenge or PHA (non-specific mitogen stimuli) for 4 days. Proliferation of CD4+ T cells was measured by $^3$H-thymidine incorporation. Data represent one of three independent experiments with four mice/group in each experiment. Data are shown as mean±SEM. Statistical significance was determined by Student's unpaired two-tailed t-test and asterisk (*) denote significant differences P≤0.05.

Whether Ni-specific CD4+ T cell proliferation was dependent on active caspase-1 activity by antigen presenting cells (APCs) was examined. CD4+ T cells from metal-sensitized C57BL/6 mice were co-incubated with mitomycin-C treated APCs (mitomycin-C inhibits cell proliferation and allows for the measurement of only the proliferation of the CD4+ T cell population) from naïve Caspase-1–/– mice in the presence or absence of Ni (FIG. 6). CD4+ T cells from vehicle and metal-sensitized C57BL/6 mice failed to proliferate in response to Ni. However, CD4+ T cells displayed significant proliferative response to phytohemaglutinin (PHA), a nonspecific mitogen stimulus. These results suggest that APCs require caspase-1/IL-1 activity to effective prime and activate Ni-specific IL-17 producing CD4+ T cells in metal-DTH.

Example 6

Ni-Specific CD4+ T Cells Require IL-1 Signaling

Figure 7A:
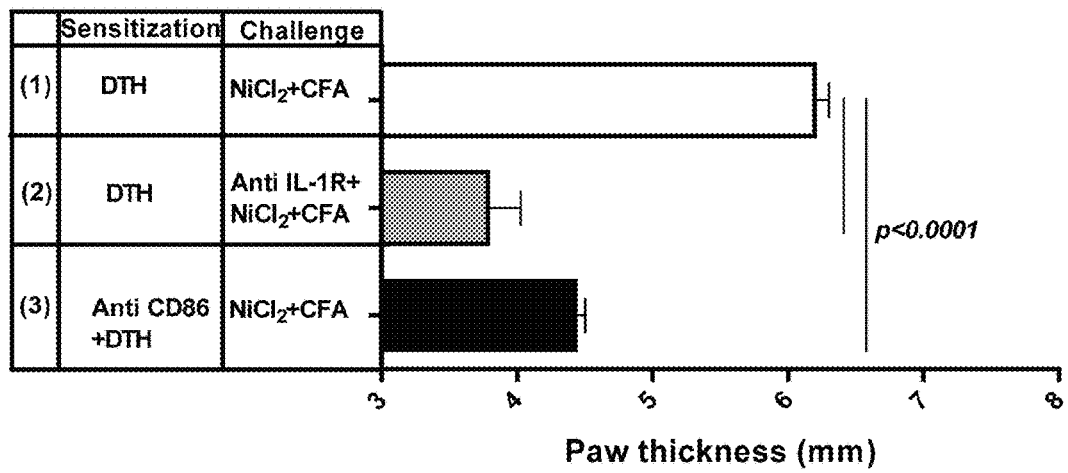
FIG. 7A. IL-1 and costimulatory signal by APCs are required for in vivo metal sensitization and for in vitro metal-reactive CD4+ T cells. DTH was determined by measuring paw thickness 48 h after challenge in C57BL/6 mice that were sensitized and challenged as indicated on day 12. Sensitized mice from group 2 received local administration of anti-mouse IL-1R (anti-mIL-1R) at the same time as challenge was delivered to the paw on day 12. Sensitized mice from group 3 received systemic i.p. injection of anti-CD86 prior to metal sensitization and every 48 hrs until day 14. At day 14, spleens were harvested.
Figure 7B:
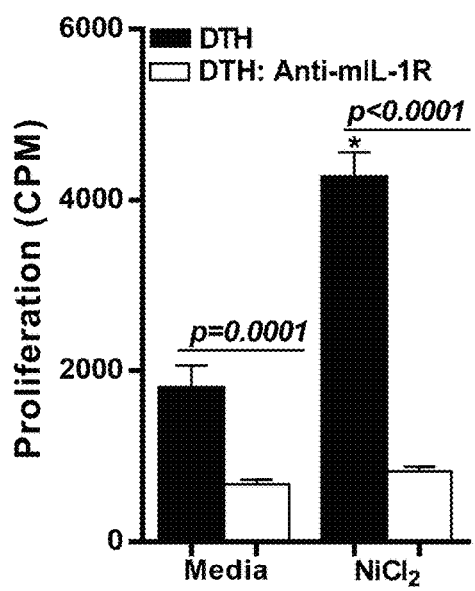
FIG. 7B. Proliferation of CD4+ T cells was measured by $^3$H-thymidine incorporation. CD4+ T cells were purified from the spleens of either DTH C57BL/6, DTH C57BL/6 mice treated locally with anti-mIL-1R and co-cultured with mitomycin-C treated naïve total spleen cells from C57BL/6 with Ni (0.001 mM) challenge for 4 days. Data represent one of three independent experiments with 3-4 mice/group in each experiment. Data are shown as mean±SEM. Statistical significance was determined by Student's unpaired two-tailed t-test (*P≤0.05).

Because caspase-1 is the rate limiting step in the inflammatory response mediated by IL-1β, and caspase-1 activity is central to this murine model of metal-DTH responses, experiments were performed to assess whether IL-1R signaling is also necessary to promote metal-DTH responses. Metal-sensitized C57BL/6 received local administration of anti-mIL-1R onto their paw in concert with challenge of Ni and CFA on day 12. Anti-IL-1R treated metal-sensitized mice displayed significantly less paw inflammation compared to metal-sensitized C57BL/6 mice (p<0.0001; FIG. 7A). Further, CD4+ T cells from anti-IL-1R treated metal-sensitized mice had significantly less proliferation in response to Ni compared with CD4+ T cells from metal-sensitized mice (p<0.0001; FIG. 7B). These results demonstrate that Ni-specific CD4+ T cell responses also require IL-1 inflammatory activity.

Example 7

Ni-Specific CD4+ T Cells Require CD86 Co-Stimulation

Figure 7C:
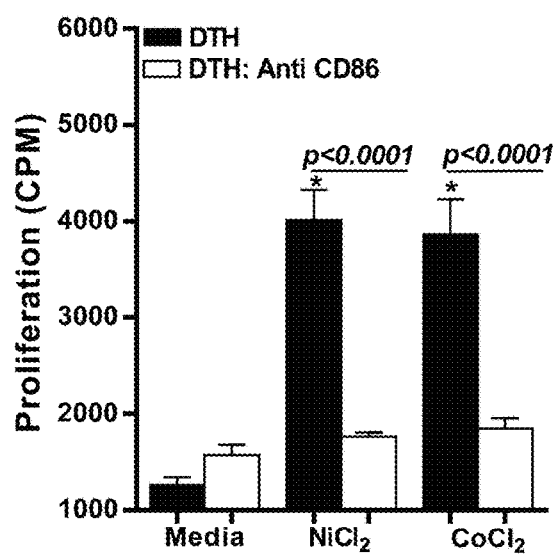
FIG. 7C. Proliferation of CD4+ T cells was measured by $^3$H-thymidine incorporation. DTH C57BL/6 or DTH C57BL/6 mice treated systemically with Anti-CD86 and co-cultured with mitomycin-C treated naïve total spleen cells from C57BL/6 with Ni (0.001 mM) or Co (0.001 mM) challenge for 4 days. Data represent one of three independent experiments with 3-4 mice/group in each experiment. Data are shown as mean±SEM. Statistical significance was determined by Student's unpaired two-tailed t-test (*P≤0.05).

Whether CD4+ T cells require co-stimulation signals for induction of metal-reactive T cells and onset of metal-DTH responses was assessed. To determine if costimulatory molecules have a central role in the T-cell-APC cross talk in this murine model of metal-DTH, costimulatory receptor CD86 was blocked in vivo. Metal-sensitized C57BL/6 mice were administrated anti-CD86 antibody in vivo during the course of metal-sensitization. Anti-CD86 treated metal-sensitized mice showed a significant decrease in paw inflammation upon Ni challenge (p<0.0001; FIG. 7A). Additionally, splenic CD4+ T-cells isolated from anti-CD86 treated metal-sensitized mice displayed significantly reduced Ni- and Co-specific T cell proliferation responses (p<0.0001) compared to metal-sensitized mice that did not receive any treatment (FIG. 7C). These results indicates that in this murine model of metal-DTH, co-stimulatory/secondary signals through CD86 by APCs are necessary for sufficient antigen signal strength during priming to elicit effector metal-reactive CD4+ T cells.

Example 8

Effect of IL-17A Blockade In Vivo on Metal-DTH Responses

Figure 8A:
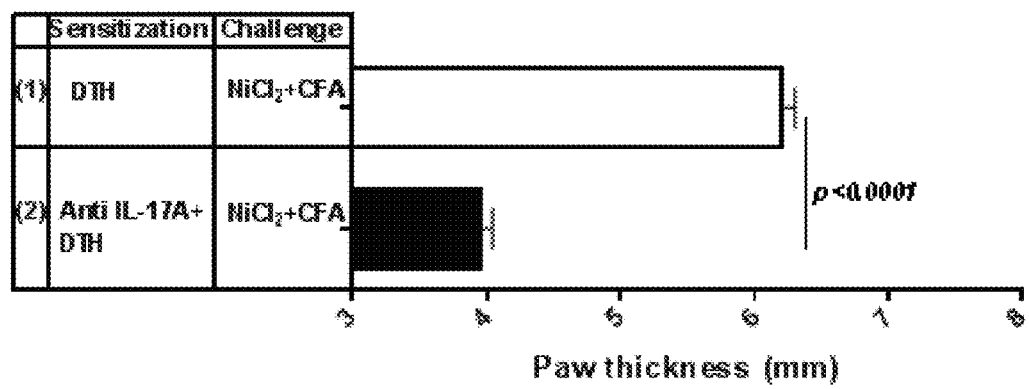
FIG. 8A. Inhibiting IL-17A bioactivity in vivo in metal-sensitized C57BL/6 mice effectively mitigates metal reactivity. DTH was determined by measuring paw thickness 48 h after challenge in C57BL/6 mice that were sensitized and challenged as indicated on day 12. Sensitized mice from group 2 received systemic ip injection of anti-IL-17A prior to metal sensitization and every 48 hrs until day 14. Data represent one of three independent experiments with 3-4 mice/group in each experiment. Data are shown as mean±SEM. Statistical significance was determined by Student's unpaired two-tailed t-test (*P≤0.05).
Figure 8B:
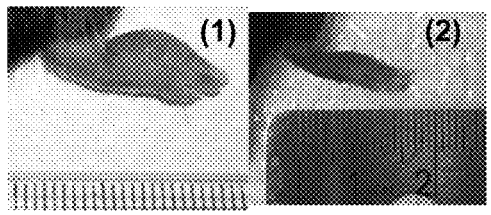
FIG. 8B. Paw thickness of C57BL/6 mice. Representative photographs of inflammatory lesions in the paws of metal-DTH treated mice on day 14. Photographs correspond to data shown in FIG. 8A.
Figure 8C:
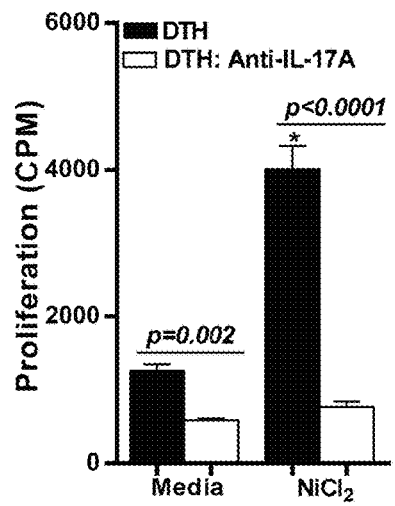
FIG. 8C. Proliferation of CD4+ T cells was measured by $^3$H-thymidine incorporation. At day 14, spleens were harvested. CD4+ T cells were purified from the spleens of either DTH C57BL/6 (black bars) or DTH anti IL-17A treated C57BL/6 mice (white bars) and co-cultured with mitomycin-C treated naïve total spleen cells from C57BL/6 with Ni (0.001 mM) challenge for 4 days. Data represent one of three independent experiments with 3-4 mice/group in each experiment. Data are shown as mean±SEM. Statistical significance was determined by Student's unpaired two-tailed t-test (*P≤0.05).
Figure 8D:
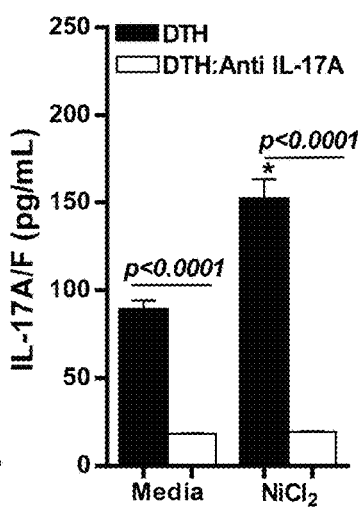
FIG. 8D. Proliferation of CD4+ T cells was measured by $^3$H-thymidine incorporation. Supernatants were harvested and assayed by ELISA for IL-17A/F. Data represent one of three independent experiments with 3-4 mice/group in each experiment. Data are shown as mean±SEM. Statistical significance was determined by Student's unpaired two-tailed t-test (*P≤0.05).
Figure 8E:
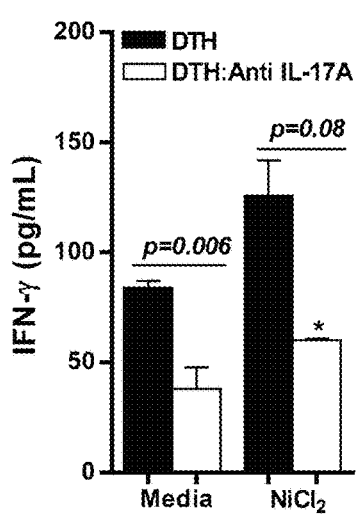
FIG. 8E. Proliferation of CD4+ T cells was measured by $^3$H-thymidine incorporation. Supernatants were harvested and assayed by ELISA for IFN-γ. Data represent one of three independent experiments with 3-4 mice/group in each experiment. Data are shown as mean±SEM. Statistical significance was determined by Student's unpaired two-tailed t-test (*P≤0.05).

Because an increase in IL-17A/F production by CD4+ T cells from metal-sensitized C57BL/6 mice correlates with increased metal-DTH responses, experiments were performed to determine whether blocking IL-17A in vivo during metal sensitization was effective at mitigating metal-DTH reactivity in vivo and in vitro. Metal-sensitized C57BL/6 mice that received systemic anti-IL-17A treatment, had significantly less paw inflammation upon Ni challenge compared with metal-sensitized mice that did not receive any biologic treatment (p<0.0001; FIGS. 8A and 8B). This observed reduction in vivo of metal-DTH severity correlated with significantly decreased CD4+ T cell proliferation responses to Ni challenge in vitro (p<0.0001; FIG. 8C). Further, CD4+ T cells from anti-IL-17A treated metal-sensitized mice displayed a significant decrease in IL-17A/F production in response to Ni (p<0.0001; FIG. 8D). However, IFN-γ secretion was significantly increased in response to Ni compared with both respective control (FIG. 8E) and to IL-17A/F secretion in response to Ni (p<0.0001; FIG. 8D vs. 8E). Taken together, these results further demonstrate that metal-DTH responses are mediated by metal-reactive IL-17A/F producing CD4+ T cells. Also, these data show that IFN-γ production is up-regulated in the absence of IL-17 activity but does not translate/correspond with metal-DTH severity. Alternatively, IFN-γ likely acts as a regulator of IL-17 inflammatory activity, and is likely a mechanism by which adaptive inflammation is controlled in metal-DTH responses.

Example 9

Figure 9A:
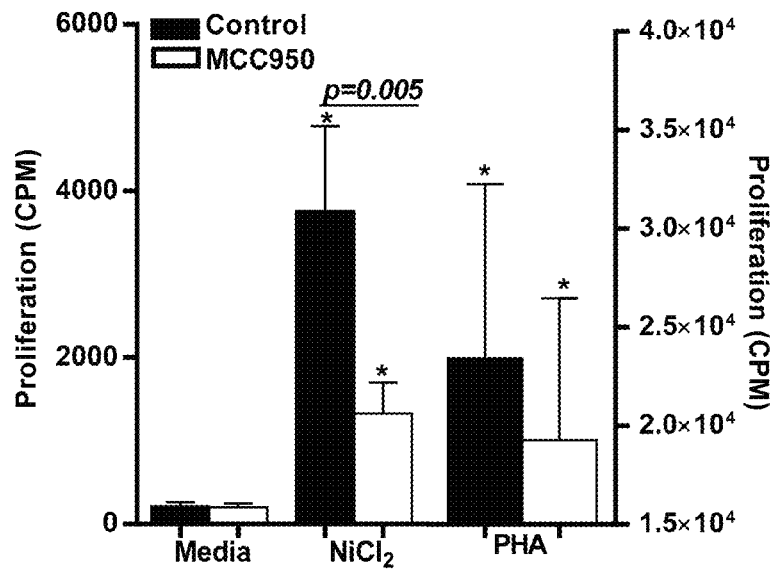
FIG. 9A. Metal-reactive lymphocytes from individuals' exhibit significant decreased metal-reactivity in the presence of inflammasome based inhibitors. Proliferation of human lymphocytes was measured by $^3$H-thymidine incorporation after 6 days of in vitro metal-challenge and in the presence of NLRP3 inflammasome inhibitor (MCC950) from n=5 individuals. Data are shown as mean±SEM. Asterisk (*) signifies statistical significance at p≤0.05 compared to respective control group as determined by paired Student's t-test.
Figure 9B:
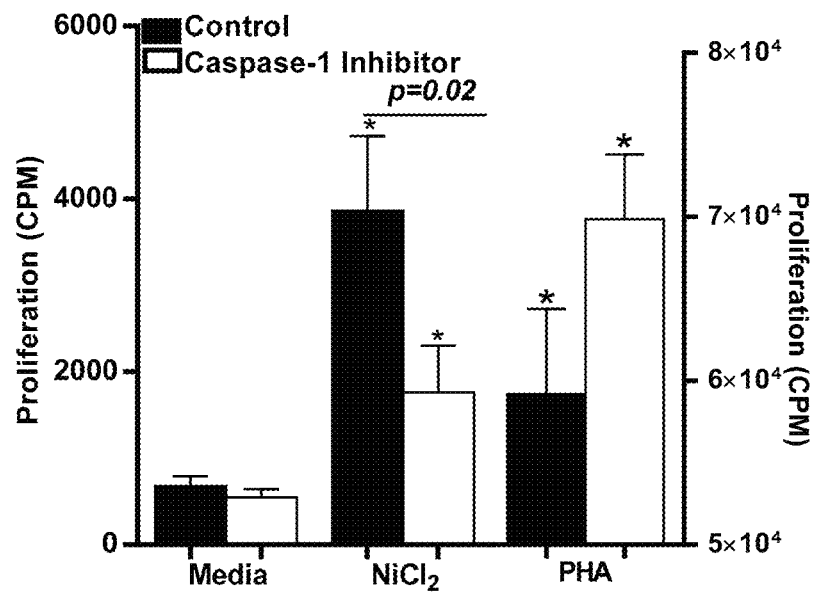
FIG. 9B. Proliferation of human lymphocytes was measured by $^3$H-thymidine incorporation after 6 days of in vitro metal-challenge and in the presence of Caspase-1 inhibitor from n=5 individuals. Data are shown as mean±SEM. Asterisk (*) signifies statistical significance at p≤0.05 compared to respective control group as determined by paired Student's t-test.

In Vitro Metal Reactivity of Human Lymphocytes is Mitigated by Blocking the NLRP3 Inflammasome Pathway The finding that metal-sensitized Nlrp3–/– and Caspase-1–/– mice displayed weakened metal-reactive CD4+ T cell activation that correlated with decreased severity of metal-DTH responses, led to testing possible therapeutic strategies by targeting the inflammasome pathway in metal-reactive individuals in vitro. Peripheral blood mononuclear cells (PBMCs) were isolated from individuals and co-incubated with an array of inflammasome pathway inhibitors in the absence/presence of metal challenge for total of 6 days, i.e., MCC950 (a NLRP3 inflammasome inhibitor), Caspase-1 inhibitor or IL-1Ra (IL-1 receptor antagonist). Subsequently, person-dependent metal-reactivity was determined by lymphocyte proliferation response to metal challenge. Ni challenged lymphocytes, proliferated vigorously, indicating these individuals are metal-reactive (n=5; p=0.006; FIG. 9A). Whereas, Ni challenged lymphocytes from the same individuals incubated with MCC950 (NLRP3 inflammasome inhibitor) showed only a weak proliferative response to Ni (FIG. 9A). Further testing using Caspase-1 inhibitor (Caspase-1 is downstream of the inflammasome complex), significantly reduced lymphocyte reactivity in response to Ni in metal-reactive individuals (n=5; p=0.02; FIG. 9B). Taken together, these results indicate that in part, NLRP3 inflammasome and caspase-1 activity are required for efficient priming of T cells to implant metals in metal reactive individuals.

Figure 10A:
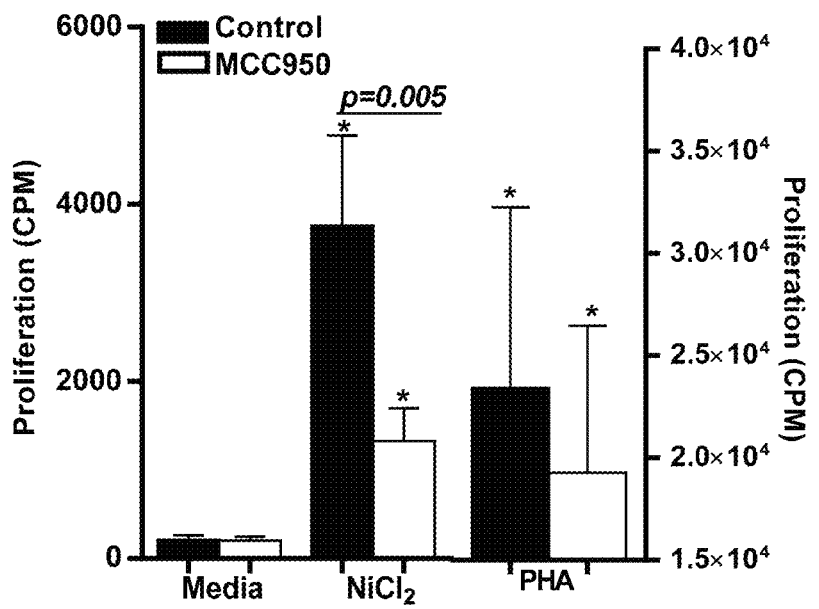
FIG. 10A. Metal-reactive lymphocytes from individuals' exhibit significant decreased metal-reactivity when IL-1 and IL-17A bioactivity is inhibited in vitro. Proliferation of human lymphocytes was measured by $^3$H-thymidine incorporation after 6 days of in vitro metal-challenge and in the presence of IL-1Ra (IL-1 receptor antagonist) from n=16 individuals. Data are shown as mean±SEM. Asterisk (*) signifies statistical significance at p≤0.05 compared to respective control group as determined by paired Student's t-test.

IL-1 targeted drugs, such as IL-1Ra (ANAKINRA®), are highly efficacious drugs for treating autoinflammatory diseases. To test whether IL-1Ra is a potential therapeutic for treating metal-DTH responses in TJA patients, metal-reactive individual lymphocytes were co-incubated in vitro with IL-1Ra in the presence of metal challenge. The addition of IL-1Ra significantly reduced lymphocyte proliferative responses to metal challenge from metal reactive individuals (n=16; p<0.001; FIG. 10A). Further, IL-1Ra was the most effective inflammasome based inhibitor (vs. MCC950 or Caspase-1 inhibitor) to mitigate lymphocyte metal reactivity because lymphocyte proliferation in response to Ni combined with IL-1Ra treatment was non-significantly different compared to media challenge. Whereas, metal challenged lymphocytes treated with either MCC950 or Caspase-1 inhibitor, displayed significant increases in cell proliferation compared to respective media control.

Example 10

Figure 10B:
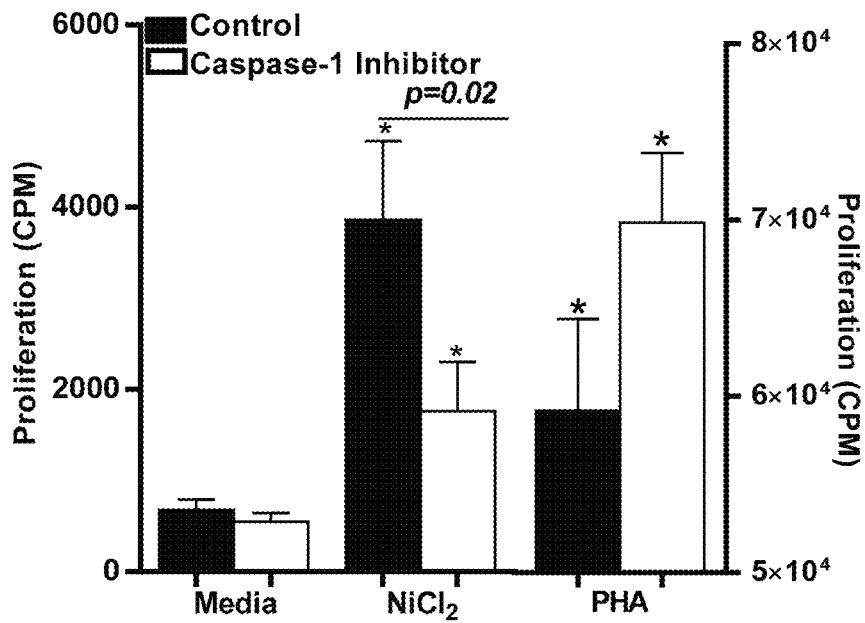
FIG. 10B. Proliferation of human lymphocytes was measured by $^3$H-thymidine incorporation after 6 days of in vitro metal-challenge and in the presence of anti-IL-17A from n=11 individuals. Data are shown as mean±SEM. Asterisk (*) signifies statistical significance at p≤0.05 compared to respective control group as determined by paired Student's t-test.

In Vitro Metal Reactivity of Human Lymphocytes is Mitigated by Blocking IL-17A Activity It was assessed whether the decrease in metal-DTH responses to anti-IL-17A treatment in vivo using this murine model, would also apply to metal reactive individuals, lymphocytes were co-incubated with anti-IL-17A in the presence of metal challenge (FIG. 10B). Metal-reactive individuals demonstrated significant decreased lymphocyte proliferation reactivity in response to Ni in the presence of anti-IL-17A (n=11; p<0.0001; FIG. 10B). However, in comparison to the tested inflammasome based inhibitors (FIGS. 9A, 9B, and 10A), anti-IL-17A treatment was not as effective in mitigating lymphocyte proliferation to metal challenge. This could be a consequence of greater immune activation to metal challenge, as exhibited by a robust lymphocyte proliferation from this subset of tested individuals (mean response to Ni=10,600 cpm) compared with other individuals tested for metal reactivity (mean response to Ni is approximately 4,000 cpm for other groups; FIGS. 9A, 9B, and 10A).

Example 11

Figure 11A:
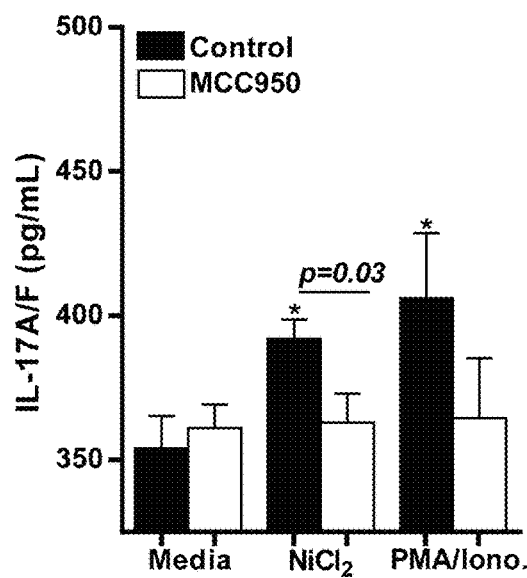
FIG. 11A. Metal-reactive lymphocytes from individuals' exhibit significant production of IL-17A/F to metal challenge. Supernatants were harvested on day 6 and assayed by ELISA for production of IL-17A/F in the absence/presence of metal challenge and/or MCC950 (NLRP3 inhibitor) from n=3 metal reactive individuals lymphocytes. Data are shown as mean±SEM. Asterisk (*) signifies statistical significance at p≤0.05 compared to respective control group as determined by paired Student's t-test.
Figure 11B:
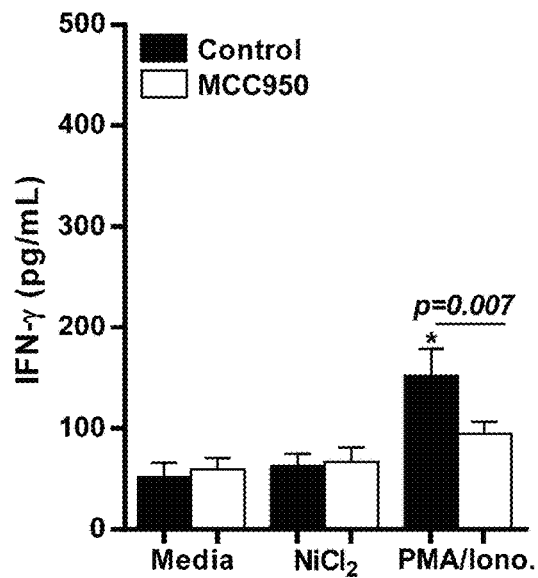
FIG. 11B. Supernatants were harvested on day 6 and assayed by ELISA for production of IFN-γ in the absence/presence of metal challenge and/or MCC950 (NLRP3 inhibitor) from n=3 metal reactive individuals lymphocytes. Data are shown as mean±SEM. Asterisk (*) signifies statistical significance at p≤0.05 compared to respective control group as determined by paired Student's t-test.
Figure 11C:
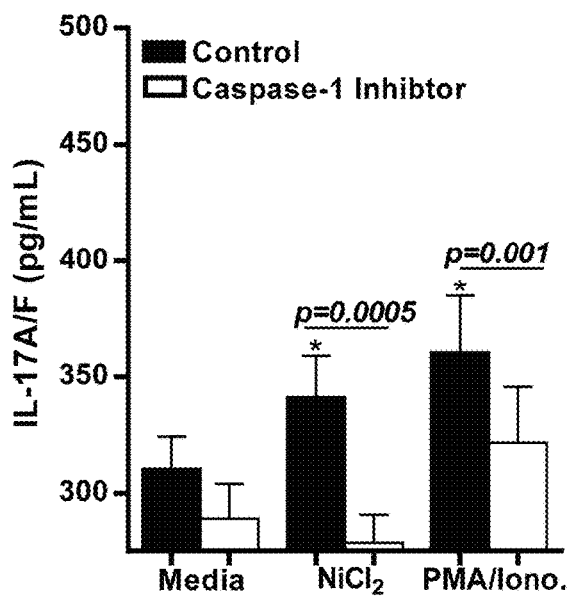
FIG. 11C. Supernatants were harvested on day 6 and assayed by ELISA for production of IL-17A/F in the absence/presence of metal challenge and/or Caspase-1 inhibitor from n=5 metal reactive individuals lymphocytes. Data are shown as mean±SEM. Asterisk (*) signifies statistical significance at p≤0.05 compared to respective control group as determined by paired Student's t-test.
Figure 11D:
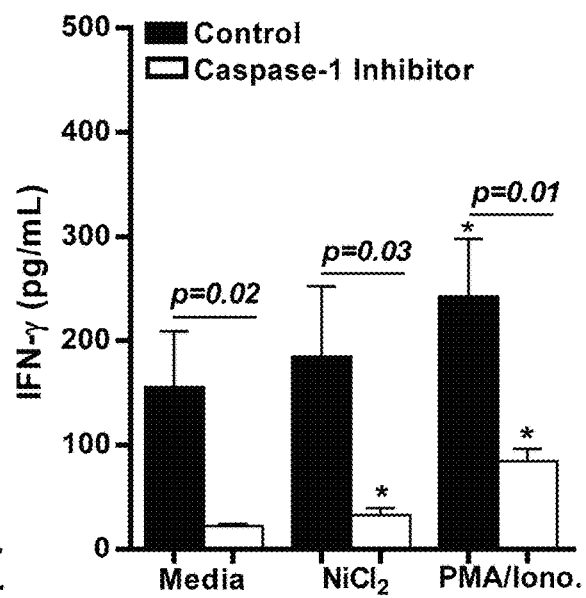
FIG. 11D. Supernatants were harvested on day 6 and assayed by ELISA for production of IFN-γ in the absence/presence of metal challenge and/or Caspase-1 inhibitor from n=5 metal reactive individuals lymphocytes. Data are shown as mean±SEM. Asterisk (*) signifies statistical significance at p≤0.05 compared to respective control group as determined by paired Student's t-test.

Metal Reactive Human Lymphocytes Exhibit Increased IL-17A/F Production, But is Suppressed by Inflammasome Based Inhibitors To evaluate the role of CD4+Th17 dependent IL-17A/F and CD4+ Th1 dependent IFN-γ production in metal reactive individuals, cytokine responses were quantified from supernatants of metal challenged lymphocytes in vitro. IL-17A/F secretion was significantly increased from metal-reactive lymphocytes to metal-challenge compared to control values (FIG. 11A). IFN-γ production from the same subset of isolated human lymphocytes was non-significantly different to metal challenge compared with control (FIG. 11B). These results were corroborated by another set of metal-reactive individuals' lymphocytes that exhibited significant increased IL-17A/F production, but not IFN-γ production to metal challenge in vitro (FIGS. 11C and 11D). However, IL-17 production from lymphocytes to metal challenge, was significantly suppressed by both MCC950 (NLRP3 inflammasome inhibitor) and Caspase-1 inhibitor (FIGS. 11A and 11C). Lymphocytic production of IFN-γ was not affected by the addition of MCC950 to metal challenge (FIG. 11B). Whereas, Caspase-1 inhibitor was a more potent inhibitor that significantly suppressed both IL-17 and IFN-γ production to metal challenge (FIGS. 11C and 11D).

Figure 12A:
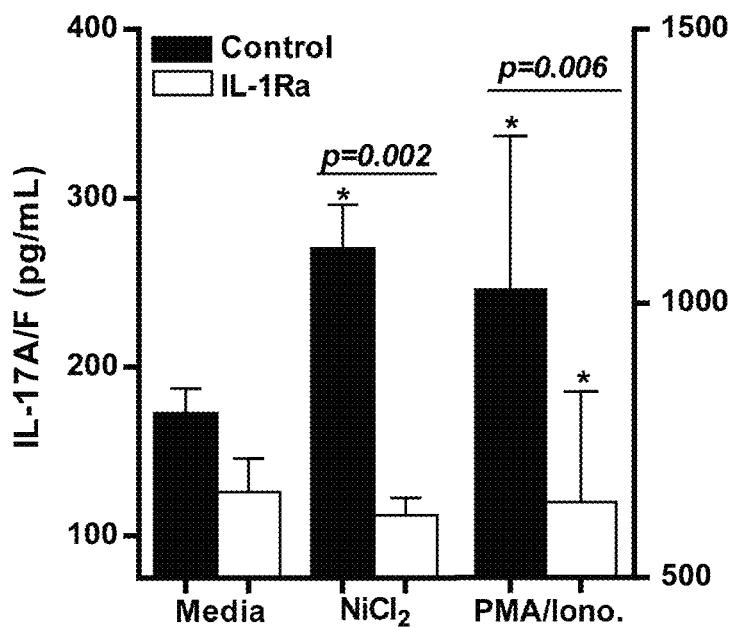
FIG. 12A. Metal-reactive lymphocytes from individuals' exhibit significant production of IL-17A/F compared with IFN-γ production to metal challenge. Supernatants were harvested on day 6 and assayed by ELISA for production of IL-17A/F secretion in the absence/presence of metal challenge and/or IL-1Ra from n=4 metal reactive individuals lymphocytes. Data are shown as mean±SEM. Asterisk (*) signifies statistical significance at p≤0.05 compared to respective control group as determined by paired Student's t-test.
Figure 12B:
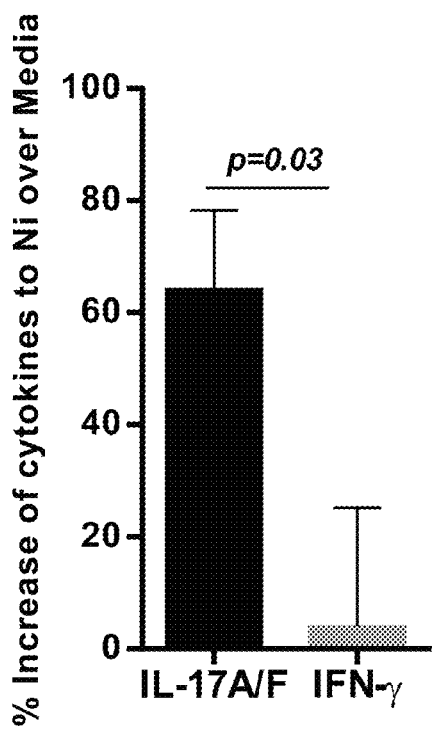
FIG. 12B. Percentage increase of secreted cytokines from n=4 metal-reactive individuals lymphocytes in response to Ni challenge over respective control values in the absence of IL-1Ra, demonstrating significant increase in IL-17A/F production compared to IFN-γ. Data are shown as mean±SEM. Asterisk (*) signifies statistical significance at p≤0.05 compared to respective control group as determined by paired Student's t-test.

Additionally, metal-reactive individual lymphocytes tested with IL-1Ra in vitro, exhibited significant increases in IL-17A/F production to metal-challenge, but IL-17 production was significantly suppressed by the presence of IL-1Ra (p=0.002; FIG. 12A). While IFN-γ lymphocyte responses to metal challenge displayed relatively low detection limits and was minimally affected by the presence of metal in vitro (FIG. 12B).

Taken together, these results demonstrate that metal reactive individuals' exhibit IL-17A/F dominant reactivity in metal-DTH responses, which can be significantly suppressed by the use of inflammasome based inhibitors. Moreover, these data demonstrate that the inflammatory environment induced by implant metals affects the function of effector T cells. Specifically, the suppressed production of IL-17 due to the presence of inflammasome inhibitors suggests that inflammatory conditions are essential for the activity of metal-specific effector T cells.

Example 12

Figure 13A:
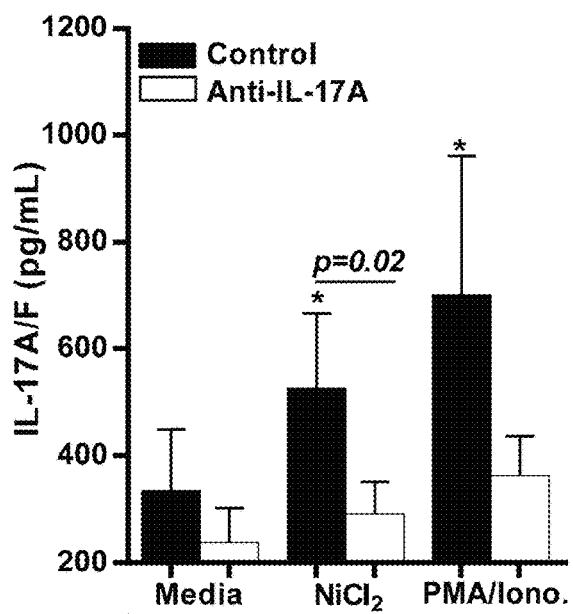
FIG. 13A. Inhibition of IL-17A signaling mitigates cytokine production in metal-reactive lymphocytes, while non-metal reactive lymphocytes do not exhibit increases in cytokine production compared to metal-reactive individuals in response to metal challenge in vitro. Anti-human IL-17A (anti-hIL-17A) treatment significantly mitigates cytokine production among metal-reactive individuals' lymphocytes to metal challenge. Production of IL-17A/F in the absence/presence of metal challenge and/or anti-hIL-17A from n=10 metal-reactive individuals. Data are shown as mean±SEM. Asterisk (*) signifies statistical significance at p≤0.05 compared to respective control group as determined by paired or unpaired Student's t-test.
Figure 13B:
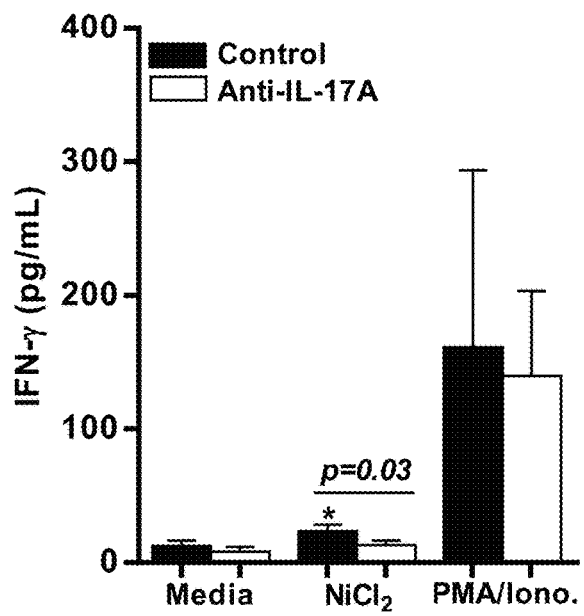
FIG. 13B. Production of IFN-γ in the absence/presence of metal challenge and/or anti-hIL-17A from n=10 metal-reactive individuals. Data are shown as mean±SEM. Asterisk (*) signifies statistical significance at p≤0.05 compared to respective control group as determined by paired or unpaired Student's t-test.

Inhibition of IL-17A Bioactivity Suppresses Cytokine Production in Metal-Reactive Lymphocytes Since metal-reactive individuals demonstrate increased IL-17 production and inhibiting IL-17 activity reduced lymphocyte proliferation reactivity to metal challenge (FIG. 10B), the effect of blocking IL-17A in vitro on cytokine production by metal reactive lymphocytes was assessed. Ni challenged lymphocytes induced significant production of IL-17A/F (n=10; p=0.03; FIG. 13A), while IFN-γ production was modestly significantly increased compared to respective control values (p=0.05; FIG. 13B). Further, IL-17A/F production was significantly greater than IFN-γ responses to Ni by metal-reactive lymphocytes (p=0.005; FIG. 13A vs. 13B). The addition of anti-IL-17A in vitro to metal challenge significantly reduced both IL-17 and IFN-γ production to metal challenge. This data further confirms that IL-17 bioactivity is centrally involved in the severity of metal-DTH responses. Also, these results show that in addition to inflammasome based inhibitors, inhibition of IL-17A bioactivity is an effective means to mitigate metal-DTH responses among metal reactive individuals.

Example 13

Figure 13C:
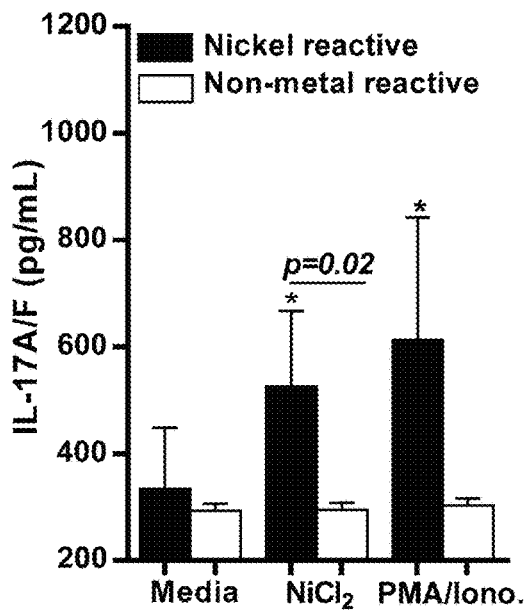
FIG. 13C. IL-17A/F production in the absence/presence of metal challenge from n=10 metal reactive individuals' lymphocytes vs. n=9 non-metal reactive individuals' lymphocytes. Data are shown as mean±SEM. Asterisk (*) signifies statistical significance at p≤0.05 compared to respective control group as determined by paired or unpaired Student's t-test.
Figure 13D:
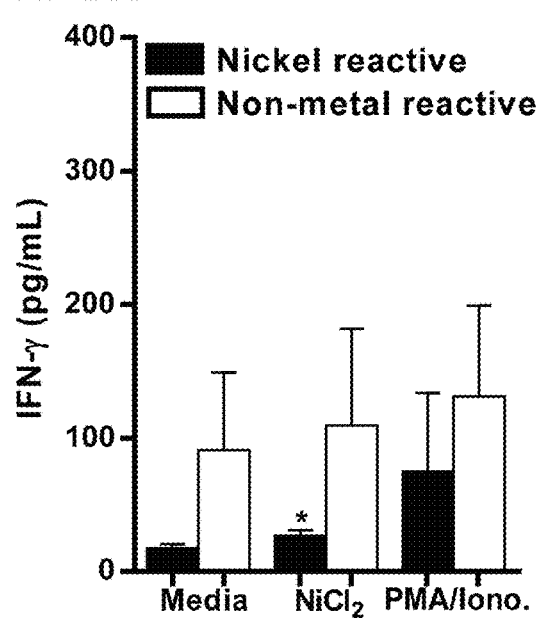
FIG. 13D. IFN-γ production in the absence/presence of metal challenge from n=10 metal reactive individuals' lymphocytes vs. n=9 non-metal reactive individuals' lymphocytes. Data are shown as mean±SEM. Asterisk (*) signifies statistical significance at p≤0.05 compared to respective control group as determined by paired or unpaired Student's t-test.

IL-17A/F and IFN-γ Production in Response to Metal Challenge in Non-Metal Reactive Individuals' Lymphocytes To further identify potential differences in susceptibility to metal-DTH responses in individuals, the cytokine prolife of non-metal reactive individuals was assessed (n=9). Non-metal reactive individuals were measured by non-significant increases in lymphocyte proliferation to metal challenge compared to respective control values as determined by a LTT assay (data not shown; SI<2, p>0.05). Metal reactive (n=10) vs. non-metal reactive individual lymphocytes demonstrated inherent differences in cytokine secretion in response to metal challenge (FIGS. 13C and 13D). IL-17 production was significantly decreased in non-metal reactive individuals (p=0.02; FIG. 13C). Whereas, IFN-γ production was non-significantly elevated in non-metal reactive individuals compared with metal reactive individuals (FIG. 13D). Thus, these data demonstrate that non-metal reactive individuals do exhibit differences in their cytokine production to metal challenge when compared to metal-reactive individuals. This may account in part, as to why a subset of TJA patients develop metal-DTH responses.

Example 14

NLRP3 inflammasome/caspase-1 activity and processed cytokine IL-1β promote adaptive IL-17 production by CD4+ T cells that drive metal-DTH responses to metal that can be released by orthopedic implants. An in vivo murine model of metal-DTH was used in this study as one way to determine the pathomechanisms(s) underlying metal-DTH responses to total joint arthroplasties (TJAs). DTH to implant metals was induced in wild-type C57BL/6, Nlrp3−/− and Caspase-1−/− mice by systemically and locally administrating clinically relevant implant metals. Ashrin et al., *J. Immunol.* 192(9): 4025-4031 (2014). Exposure to metal ions in vivo requires processing by an active inflammasome/caspase-1 complex in innate immune cells to induce metal-specific effector T cells in metal-DTH. Inhibition of the inflammasome complex suppressed metal-reactive CD4+ T cells and corresponding IL-17A/F responses to implant metal, which significantly weakened metal-DTH responses both in vivo and in vitro. Furthermore, metal-sensitized Caspase-1−/− mice exhibited increased IFN-γ production, and suppressed IL-17 production. Despite, this increase in IFN-γ expression it did not result in metal-DTH inflammation and lymphocyte proliferation responses. This data supports the general hypothesis that inflammasome activity is required for IL-17 secreting CD4+ Th17 cells. More specifically, the results of this study support the hypothesis that inflammasome activation complex is central to the pathogenesis of Th17 mediated metal-DTH responses to TJAs.

Figure 14:
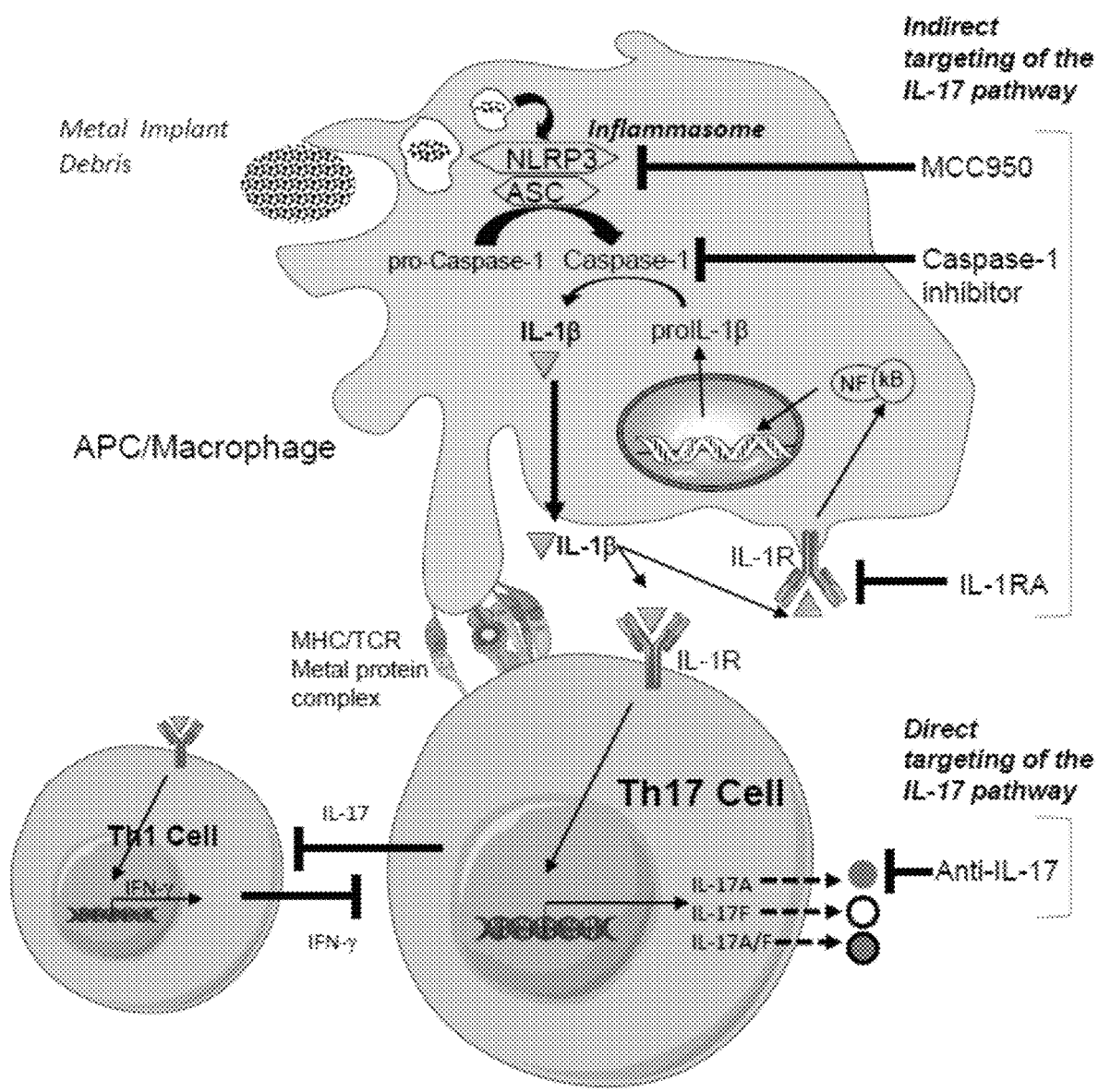
FIG. 14. Indirect and/or direct targeting of the IL-17 pathway to mitigate metal-DTH reactivity. A representation of NLRP3 inflammasome activation in APCs by phagocytosis of metal implant debris, which promotes IL-1β signaling and the induction of a Th17-cell phenotype. Caicedo et al., *J. Orthop. Res.* 31(10): 1633-1642 (2013). And the possible biological targets that indirectly (via the inflammasome pathway) and directly (anti-IL-17A) target the IL-17 signaling pathway to decrease the severity of metal-DTH immune reactivity given these findings. IFN-γ is a signature cytokine of Th1 cells and is an important Th1 inducer, that can suppress Th17, Th2, and Treg cell differentiation. Zhu et al., *Annu. Rev. Immunol.* 28: 445-489 (2010). While IL-1 and IL-17 are important for Th17 cell differentiation and can repress Th1 cell differentiation. Under metal-DTH responses, IL-1 and IL-17 are highly secreted, indicating more of a Th17 cells phenotype for metal-DTH immune reactivity.

The release of particles and metal ions from certain types of metallic orthopedic implants can cause >100 fold elevations in systemic level of metals such as cobalt and chromium. Hart et al., *J. Bone Joint Surg. Am.* 96(13): 1091-1099 (2014); Hallab et al., *J. Orthop. Res.* 31(2): 173-182 (2013); Kwon et al., *J. Arthroplasty* 26(4): 511-518 (2011). It has been previously shown that both particulate and soluble implant debris elicit innate inflammatory immune responses mediated by the NLRP3 inflammasome. Caicedo et al., *J. Biomed. Mater. Res. A* 93(4): 1312-1321 (2010); Caicedo et al., *J. Orthop. Res.* 27(7): 847-854 (2008); Samelko et al., *PLoS One* 11(7): e0160141 (2016); Caicedo et al., *J. Orthop. Res.* 31(10): 1633-1642 (2013). DTH reactions to TJAs has been histologically identified by increased per-implant lymphocyte infiltration/accumulation surrounding the peri-implant tissue; including CD3+ and CD4+ T lymphocytes as well as innate immune cells such as CD11c+ macrophages. Perry et al., *Br. J. Rheumatol.* 34(12): 1127-1134 (1995); Torgersen et al., *Eur. J. Oral Sci.* 103(1): 46-54 (1995). However, there is a lack of therapeutic options for implant associated metal-DTH pathology. Given the increasing number of TJAs performed per year and the decreasing age of TJA patients, a better understanding of the interplay between the innate and adaptive immune system is central to for understanding metal-DTH etiology/pathogenesis and effective therapeutic strategies (FIG. 14).

Therefore, to determine the pathomechanism(s) underlying metal-DTH responses to TJAs, an in vivo murine model of metal-DTH was used. In vivo experiments using metal-sensitized wild-type C57BL/6 exhibited metal-DTH reactivity that corresponded with robust CD4+ T cell proliferation and increased IL-17A/F responses to metal re-challenge. While metal-sensitized Nlrp3−/− and Caspase-1−/− mice resulted in significant mitigated CD4+ T cell responsiveness to metal re-challenge as measured by proliferation and IL-17A/F production. Surprisingly, metal-sensitized Caspase-1"/" mice revealed enhanced protection from developing metal reactivity compared to NLRP3−/− mice. These results indicate: (1) that the inhibition of the inflammasome pathway is an effective means to mitigate both the sensitization and elicitation phases of metal-DTH responses, and (2) downstream components of the inflammasome (i.e., Caspase-1) demonstrated a greater effect on modulating/inducing T-cell effector mediated immune reactivity to metal allergens (FIG. 14).

In assessing cytokine expression by CD4+ T cells from metal-sensitized C57BL/6 mice, a significant increased expression of IL-17A/F was observed but not of IFN-γ in response to metal challenge in vitro. In contrast, CD4+ T cells from metal-sensitized Caspase-1−/− mice exhibited significant increases in IFN-γ production but not of IL-17A/F production. To further assess the role of IL-17, a neutralizing antibody against IL-17A was administered in vivo during the course of metal-DTH induction in C57BL/6 mice. Metal-DTH responses are dependent on IL-17 given that neutralization of IL-17 significantly inhibited metal-DTH responses, as measured by in vivo paw inflammation and in vitro T cell proliferation responses (FIG. 8). These findings indicate that in addition to inflammasome signaling, IL-17 plays a crucial role in the development of metal-DTH responses to TJAs by activating metal-specific CD4+ T cell responses. Nakae et al., *Immunity* 17(3): 375-387 (2002); He et al., *J. Immunol.* 177(10): 6852-6858 (2006).

Several autoimmune disease models (i.e., experimental autoimmune encephalomyelitis (EAE) and collagen-induced arthritis (CIA)) have demonstrated that IFN-γ has the ability to downregulate symptoms of disease in animal models that use CFA in the induction of the disease. Vermeire et al., *J. Immunol.* 158(11): 5507-5513 (1997); Ferber et al., *J. Immunol.* 156(1): 5-7 (1996); Avau et al., *Arthritis Rheumatol.* 66(5): 1340-1351 (2014); Chu et al., *Arthritis Rheum.* 56(4):1145-1151 (2007). Further, it was discovered that in the absence of IFN-γ, there is a loss of control over IL-17 dominated innate and adaptive immune responses. Id.; Chang and Dong, *Cell Res.* 17(5): 435-440 (2007); Liang et al., *J. Immunol.* 179(11): 7791-7799 (2007). These findings show that metal-sensitized Caspase-1−/− mice did not develop metal-DTH responses but exhibited elevated IFN-γ expression, and implies that despite the pro-inflammatory nature of IFN-γ, it plays a non-activating or protective role in metal-DTH pathology.

The inflammasome is known to detect multitude of danger signals, such as endogenous molecules released during tissue damage that induce innate immune activation and inflammation. Consequently, the development of DTH immune reactivity to orthopedic metal(s) likely involves a one-two punch where implant debris acts as a danger signal to activate innate immune NLRP3 inflammasome and antigenic to elicit effector T-cells in the sensitization phase.

Consequently, effector T-cells induce inflammation and promote progressive tissue damage at the per-implant interface during the elicitation phase and upon re-exposure to metal-allergen. This was supported in this study by assessing histological differences from the paw tissue of metal-sensitized C57BL/6 mice. The common, although qualitative feature was the association of lymphocytic infiltration (i.e., aseptic lymphocyte associated vasculitis, ALVAL) corresponding with increased paw erythema and inflammation to metal re-challenge (FIG. 1). These results are similar to histological evaluations of failed metal-on-metal total hip replacements that exhibited increased per-implant lymphocyte infiltration/accumulation surrounding the per-implant tissue ALVAL. Willert et al., *J. Bone Joint Surg. Am.* 87(1): 28-36 (2005); Basketter et al., *Contact Dermatitis* 28: 15-25 (1993); Cramers and Lucht, *Acta Orthopedica Scandinavia* 8: 245-249 (1977); Fisher, *Current Contact News* 19: 285-295 (1977); Aroukatos et al., *Clin. Orthop. Relat. Res.* 468(8): 2135-2142 (2010); Thomas et al., *Allergy* 64(8): 1157-1165 (2009); Kwon et al., *J. Orthop. Res.* 28(4): 444-450 (2010); Davies et al., *J. Bone Joint Surg. Am.* 87(1): 18-27 (2005). Additionally, it was determined co-stimulatory molecule CD86 expressed by antigen presenting cells (APCs) plays a central role during the initiation of T-cell immune responses to implant metals. In vivo blockade of CD86 during metal-sensitization lead to decreased metal-DTH reactivity that corresponded with weakened T cell proliferative responses to metal challenge (FIG. 7). These data strongly indicate that in vivo exposure to implant metals elicits lymphocyte activation and that APC co-stimulation is crucial to the development of metal-DTH lymphocytic immune responses in the murine model of metal-DTH.

The respective roles of Th1, Th2 and Th17 cells in metal-DTH reactions have yielded conflicting data, since each have been indicated to play a role. Borg et al., *Arch. Dermatol. Res.* 292(6): 285-291 (2000); Falsafi-Amin et al., *Int. Arch. Allergy Immunol.* 23(2): 170-176 (2000); Jakobson et al., *Br. J. Dermatol.* 147(3): 442-449 (2002); Minang et al., *Clin. Exp. Immunol.* 146(3): 417-426 (2006); Hallab et al., *J. Orthop. Surg.* 3: 6 (2008); Bechara et al., *J. Invest. Dermatol.* 137(10): 2140-2148 (2017); Dyring-Andersen et al., *Contact Dermatitis* 68(6): 339-347 (2013); Zhao et al., *Br. J. Dermatol.* 161(6): 1301-1306 (2009). Possible explanations for the differences among the studies was the use of patch test vs. LTT assay to determine metal reactivity, and various methods of measuring cytokine expression from blood and skin-derived lymphocytes. Further, studies examining human allergic contact dermatitis reactions to metals is not similar to metal-DTH responses to TJAs, given that the location of the immune response is uniquely different, resulting in differential activation of effector T cell phenotypes which may in part be responsible for observed differences. In this regard, these results demonstrate that lymphocytes isolated from metal-reactive individuals produced cytokines that correlated with those produced from the model of metal-sensitized C57BL/6 mice and support a Th-17 phenotype dominated response. Kondo et al., *J. Invest. Dermatol.* 105(3): 334-338 (1995). These data are important in building a consensus of reported DTH pathomechanisms responses that is central to hypothesis validation over time. Importantly, the histological manifestations of metal-DTH reactions were similar, corresponding with lymphocytic infiltrations identified in failed MoM THAs. Metal-reactive lymphocytes treated with inflammasome based inhibitors or anti-IL-17A antibody, exhibited significant decrease in T cell proliferation responses and cytokine production to metal challenge in vitro. These data further support the hypothesis that inflammasome/caspase-1 and IL-17A/F bioactivity is required for the activation of metal-reactive T-cells and the pathogenesis of metal-DTH responses.

These studies did not determine whether metal sensitive individuals have genetic/epigenetic variations in NLPR3 inflammasome, IL-17 or anti-inflammatory (i.e., IL-10, IL-1Ra, IL-4 etc.) gene expression that render them susceptible to metal-DTH immune reactivity vs. non-metal sensitive individuals. Lee et al., *PLoS One* 12(10): e0186351 (2017). However, these in vitro results imply that among metal-reactive lymphocytes that either inhibition of the inflammasome or IL-17 pathway is a viable therapeutic strategy to prevent/mitigate implant debris related metal-DTH responses. It is important to note that use of inhibitors in vitro can cause potential off-target effects that may in part account for reduced metal-reactivity yet remains potential therapeutic candidates. Additional studies performed with TJR patients that exhibit metal-sensitivity and/or ALVAL, are needed to further establish the relative contribution/role of IL-17 and of Th17 cells in metal-DTH responses and implant outcomes. In general, these results may help understand disparate clinical responses to TJAs and better individualize therapy choices.

These findings suggest that the transition from metal-DTH resistance to susceptibility may be facilitated by active danger signaling, i.e., inflammasome/caspase-1 signaling, and the resulting production of IL-17A/F. This indicates that local release of IL-1β and IL-17A/F near the peri-implant tissue work in concert to promote effector T cell immune reactivity that elicit metal-DTH responses to TJAs. This investigation raises the possibility that excessive NLRP3 inflammasome innate immune reactivity to metal degradation products in vivo can lead to DTH-responses through CD4+ T cell release of IL-17A/F. Targeting the nexus of inflammasome or Th17 signaling (e.g., IL-1Ra and/or anti-IL-17) may be a potential treatment option(s) for metal-DTH reactions to TJAs or metal exposure in general.

What is claimed:

1. A method for treating an adverse immune reaction to metal debris, metal induced delayed type hypersensitivity, or inflammatory osteolysis in a subject in need thereof comprising administering an inhibitor of IL-17 activity, wherein the adverse immune reaction to metal debris, metal induced delayed type hypersensitivity, or inflammatory osteolysis is caused by orthopedic metal implant debris.

2. The method of claim 1, wherein said inhibitor is an effective amount of one or more anti-cytokine antibodies, anti-receptor antibodies, soluble receptors, receptor inhibitors, or blocking agents to the subject.

3. The method of claim 2, wherein the anti-cytokine antibodies, anti-receptor antibodies, soluble receptors, receptor inhibitors, or blocking agents comprise anti-IL-17, anti-IL-17A, anti-IL-17F, anti-IL-17A/F, soluble IL-17 receptors, IL-17 receptor inhibitors, or combinations thereof.

4. The method of claim 2, wherein the anti-cytokine antibodies, anti-receptor antibodies, soluble receptors, receptor inhibitors, or blocking agents comprise secukinumab, ixekizumab, brodalumab, or combinations thereof.

5. The method of claim 2, wherein the anti-cytokine antibodies, anti-receptor antibodies, soluble receptors, receptor inhibitors, or blocking agents, are co-administered.

6. The method of claim 2, wherein administration of the inhibitor occurs within about 0.5 hour to about 30 days of onset of the adverse immune reaction to metal debris, metal induced delayed type hypersensitivity, or inflammatory osteolysis.

7. The method of claim 2, wherein administration of the inhibitor comprises parenteral administration.

8. The method of claim 2, wherein administration of the inhibitor comprises intravenous, intraarterial, intramuscular, intraarticular, intradermal, subcutaneous, or intraperitoneal administration.

9. The method of claim 2, wherein administration of the inhibitor comprises intravenous administration.

10. The method of claim 1, wherein the subject is a human.

11. The method of claim 1, wherein the orthopedic metal implant debris comprises nickel, cobalt, or chromium.

12. The method of claim 1, wherein the orthopedic metal implant is associated with total joint arthroplasty.

13. The method of claim 1, wherein the adverse immune reaction to metal debris, metal induced delayed type hypersensitivity, or inflammatory osteolysis is identified histologically as aseptic lymphocyte-dominated vasculitis-associated lesions (ALVAL) in periprosthetic tissue.

14. A method for depleting a subject's systemic levels of IL-17 or blocking a IL-17 receptor comprising contacting IL-17 or IL-17 receptors with anti-IL-17, anti-IL-17A, anti-IL-17F, anti-IL-17A/F, anti-IL-1, anti-IL-1β, anti-IL-1R, soluble IL-17 receptors, IL-17 receptor inhibitors, or combinations thereof, wherein the subject is experiencing an adverse immune reaction to metal debris, metal induced delayed type hypersensitivity, or inflammatory osteolysis that is caused by orthopedic metal implant debris.

15. The method of claim 14, wherein the contacting comprises parenteral administration of one or more of anti-cytokine antibodies, anti-receptor antibodies, soluble receptors, receptor inhibitors, or blocking agents.

16. The method of claim 15, wherein the parenteral administration comprises intravenous, intraarterial, intramuscular, intraarticular, intradermal, subcutaneous, or intraperitoneal administration.

17. A method for inhibiting IL-17 activity in a subject experiencing adverse immune reaction to metal debris, metal induced delayed type hypersensitivity, or inflammatory osteolysis by the administration of one or more anti-cytokine antibodies, anti-receptor antibodies, soluble receptors, receptor inhibitors, or blocking agents of IL-17 or IL-17 receptors to the subject, wherein the adverse immune reaction to metal debris, metal induced delayed type hypersensitivity, or inflammatory osteolysis is caused by orthopedic metal implant debris.

18. The method of claim 17, wherein the anti-cytokine antibodies, anti-receptor antibodies, soluble receptors, receptor inhibitors, or blocking agents comprise anti-IL-17, anti-IL-17A, anti-IL-17F, soluble IL-17 receptors, IL-17 receptor inhibitors, or combinations thereof.

19. The method of claim 17, wherein the anti-cytokine antibodies, anti-receptor antibodies, soluble receptors, receptor inhibitors, blocking agents comprise secukinumab, ixekizumab, brodalumab, or combinations thereof.

20. The method of claim 17, wherein the anti-cytokine antibodies, anti-receptor antibodies, soluble receptors, receptor inhibitors, or blocking agents are co-administered.

21. A method for blocking intracellular effects of IL-17 or IL-17R, in a subject, comprising administering anti-IL-17, anti-IL-17A, anti-IL-17F, anti-IL-17A/F, soluble IL-17 receptors, IL-17 receptor inhibitors, or combinations thereof, wherein the subject is experiencing an adverse immune reaction to metal debris, metal induced delayed type hypersensitivity, or inflammatory osteolysis that is caused by orthopedic metal implant debris.

* * * * *

UNITED STATES PATENT AND TRADEMARK OFFICE
CERTIFICATE OF CORRECTION

PATENT NO. : 11,352,421 B2
APPLICATION NO. : 16/216159
DATED : June 7, 2022
INVENTOR(S) : Hallab et al.

It is certified that error appears in the above-identified patent and that said Letters Patent is hereby corrected as shown below:

In the Claims
Column 38, Line 8, after "ant-IL-17F," insert --anti-IL-17A/F,--

Signed and Sealed this
Eleventh Day of October, 2022

Katherine Kelly Vidal
*Director of the United States Patent and Trademark Office*